US007056731B1

(12) United States Patent
Thomae et al.

(10) Patent No.: US 7,056,731 B1
(45) Date of Patent: Jun. 6, 2006

(54) SULFOTRANSFERASE SULT2A1 SEQUENCE VARIANTS

(75) Inventors: Bianca A. Thomae, Rochester, MN (US); Eric D. Wieben, Rochester, MN (US); Richard M. Weinshilboum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 435 days.

(21) Appl. No.: 10/177,570

(22) Filed: Jun. 21, 2002

Related U.S. Application Data

(60) Provisional application No. 60/300,165, filed on Jun. 22, 2001.

(51) Int. Cl.
*C12N 15/11* (2006.01)
*C12N 15/54* (2006.01)
*C12N 9/10* (2006.01)

(52) U.S. Cl. ............... 435/320.1; 536/23.2; 536/24.31; 435/193

(58) Field of Classification Search ............... 536/23.2, 536/24.31; 435/193, 320.1
See application file for complete search history.

(56) References Cited

U.S. PATENT DOCUMENTS

| 5,451,683 | A | 9/1995 | Barrett et al. |
| 5,733,729 | A | 3/1998 | Lipshutz et al. |
| 5,770,722 | A | 6/1998 | Lockhart et al. |

FOREIGN PATENT DOCUMENTS

| WO | WO 98/20019 | 5/1998 |
| WO | WO 99/57318 | 11/1999 |
| WO | WO 99/64630 | 12/1999 |
| WO | WO 00/20605 | 4/2000 |
| WO | WO 01/00829 | 1/2001 |

OTHER PUBLICATIONS

GenBank Accession No. U08024 (Apr. 1994).
GenBank Accession No. U13056 (May 1995).
GenBank Accession No. U13057 (May 1995).
GenBank Accession No. U13058 (May 1995).
GenBank Accession No. U13059 (May 1995).
GenBank Accession No. U13060 (May 1995).
GenBank Accession No. U13061 (May 1995).
Adjei and Weinshilboum, "Catecholestrogen Sulfation: Possible Role in Carcinogenesis. " *Biochem. Biophys. Res. Comm.*, 2002, 292:402-408.
Barrett-Connor et al., "A Prospective Study of Dehydroepiandrosterone Sulfate, Mortality, and Cardiovascular Disease, " *N. Engl. J. Med.*, 1986, 315:1519-1524.

Barrou et al., "Actions De La Déhydropiandrostérone Possibles Liens Avec Le Viellissement." *Presse Med.*, 1996, 25:1885-1889,(includes English summary).
Barrou et al., "Dehydroepiandrosterone (DHEA) and aging," *Arch Gerontol. Geriatrics* , 1997, 24:233-241.
Brind, "Spotlight on DHEA: A marker for progression of HIV infection?" *J. Lab. Clin Med.*, 1996,127:522-523.
Campbell et al. "Human Liver Phenol Sulfotransferase: Assay Conditions. Biochemical Properties and Partial Purification of Isozymes of the Thermostable Form, " *Biochem. Pharmacol.*, 1987, 36(9):1435-1446.
Cleland, "Computer Programmes for Processing Enzyme Kinetic Data, " *Nature*, 1963, 198:463-465.
de la Torre et al., "Blood cortisol and dehydroepiandrosterone sulphate (DHEAS) levels and CD4 T cell counts in HIV infection," *Clin Exp. Rheumatol.*, 1997, 15:87-90.
Guatelli et al, "Isothermal, *in vitro* amplification of nucleic acids by a multienzyme reaction modeled after retroviral replication," *Proc. Natl. Acad. Sci. USA*, 1990, 87:1874-1878.
Hacia et al., "Detection of heterozygous mutations in *BRCA1* using high denisty oligonucleotide arrays and two-colour fluorescence analysis," *Nature Genetics*, 1996, 14:441-447.
Halushka et al., "Patterns of single-nucleotide polymorphisms in candidate genes for blood-pressure homeostasis," *Nature Genetics*, 1999, 22:239-247.
Hartl and Clark, *Principles of Population Genetics*, Third Edition, 1997, Sinauer Associates, Inc., Sunderland, MA, pp. 95-109.
Ho et al., "Site-directed mutagenesis by overlap extension using the polymerase chain reaction," *Gene* , 1989, 77:51-59.
Huse et al., "Generation of a Large Combinatorial Library of the Immunoglobulin Repertoire in Phage Lambda," *Science*, 1989, 246:1275-1281.
Hyrup and Nielsen, "Peptide Nucleic Acids (PNA): Synthesis, Properties and Potential Applications," *Bioorganic & Medical Chemistry*, 1996, 4:5-23.
Myakishev et al., "High-Throughput SNP Genotyping by Allele-Specific PCR with Universal Energy-Transfer-Labeled Primers," *Genome Res*, 2001, 11:163-169.
Prince et al., "Robust and Accurate Single Nucleotide Polymorphism Genotyping by Dynamic Allele-Specific Hybridization (DASH): Design Criteria and Assay Validation, " *Genome Res.*, 2001, 11:152-162.

(Continued)

*Primary Examiner*—Rebecca Prouty
(74) *Attorney, Agent, or Firm*—Fish & Richardson, P.C., P.A.

(57) ABSTRACT

Isolated sulfotransferase nucleic acid molecules that include a nucleotide sequence variant and nucleotides flanking the sequence variant are described, as well as sulfotransferase allozymes. Methods for determining if a mammal is predisposed to a heart condition or cancer also are described.

5 Claims, 5 Drawing Sheets

OTHER PUBLICATIONS

Schafer and Hawkins, "DNA variation and the future of human genetics," *Nature Biotechnol.*, 1998, 16:33-39.

Schulz and Nyce, "Inhibition of protein farnesyltransferase: a possible mechanism of tumor prevention by dehydroepiandrosterone sulfate," *Carcinogenesis*, 1994, 15(11):2649-2652.

Shastry, "Gene disruption in mice: Models of development and disease." *Mol. Cell. Biochem.*, 1998, 181:163-179.

Stoneking et al., "Population Variation of Human mtDNA Control Region Sequences Detected by Enzymatic Amplification and Sequence-specific Oligonucleotide Probes." *Am. J. Hum. Genet.*, 1991, 48:370-382.

Summerton and Weller, "Morpholino Antisense Oligometers: Design, Preparation, and Properties." *Antisense & Nucleic Acid Drug Development*, 1997, 7:187-195.

Terwilliger and Ott, *Handbook of Human Genetic Linkage*, 1994, The Johns Hopkins University Press, Baltimore and London, pp. 188-198.

Thomae et al., "Human sulfotransferase SULT2A1 pharmacogenetics: genotype-to-phenotype studies," *Pharmacogenomics J.*, 2002, 2:48-56.

Underhill et al., "Detection of Numerous Y Chromosome Biallelic Polymorphisms by Denaturing High-Performance Liquid Chromatography," *Genome Res.*, 1997, 7:996-1005.

Van Loon and Weinshilboum, "Thiopurine Methyltransferase Isozymes in Human Renal Tissue," *Drug Metab. Dispos.*, 1990, 18(5):632-638.

Van Loon et al., "Human Kidney Thiopurine Methyltransferase." *Biochem. Pharmacol.*, 1992, 44(4):775-785.

Wakayama et al., "Full-term development of mice from enucleated oocytes injected with cumulus cell nuclei," *Nature*, 1998, 394:369-374.

Weiss, "Hot Prospect for New Gene Amplifier," *Science*, 1991, 254:1292-1293.

Wilkinson, "Statistical Estimations in Enzyme Kinetics." *Biochem. J.*, 1961, 80:324-332.

Wilmut et al., "Viable offspring derived from fetal and adult mammalian cells.", *Nature* 1997. 385:810-813.

Wong et al., "Human GM-CSF: Molecular Cloning of the Complementary DNA and Purification of the Natural and Recombinant Proteins," *Science*, 1985, 228:810-815.

Wood et al., "Human Liver Thermolabile Phenol Sulfotransferase: cDNA Cloning, Expression and Characterization," *Biochem. Biophys. Res. Comm.*, 1994, 198(3):1119-1127.

Wood et al., "Human Dehydroepiandrosterone Sulfotransferase Pharmacogenetics: Quantitative Western Analysis and Gene Sequence Polymorphisms," *J. Steroid Biochem. Molec. Biol.*, 1996, 59(5/6):467-478.

Pedersen et al., "Crystal Structure of SULT2A3, Human Hydroxysteroid Sulfotransferase," *FEBS Letters*, 2000, 475:61-64.

Cibelli et al., "Cloned Transgenic Calves Produced from Non-quiescent Fetal Fibroblasts," *Science*, 1998, 280:1256-1258.

|  |  |  |  |  | Accession # |
|---|---|---|---|---|---|
| 1 | gggttcatgc | cattctcctg | cctcagcctc | ctgagtagct gggactacag | U13056 |
| 51 | gcacccgcca | ccacgcccgg | ctaattttt | gtatttttag tagagacggg | 5'-FR and |
| 101 | gtttcaccgt | gttagccagg | atggtctcga | tctcctgacc tcgtgatccg | Exon 1 |
| 151 | cccgcctcgg | cctcccaaag | tgctgggatt | acaggcgtga gcaccacacc | |
| 201 | gtgcccagac | caagaatgaa | ggttttgta | aagatttctg ttcagtgttt | |
| 251 | tgcaaggtaa | aattctaggc | acgttttccc | tgaagttatg tgtatgtgag | |
| 301 | tattctcatt | cttcccaact | tgcctttgaa | gagtgaaaaa acattattat | |
| 351 | caagtagact | tctattcagc | ttttgctcct | gccctgctgt ttatccctta | |
| 401 | agaatgagtt | tcttggactt | tcccaatatg | tgattttttt ttcccattta | |
| 451 | gaatggtgat | tttaaatgtg | tgagtgcatg | cattatctta tctcagatat | |
| 501 | ttgcaccccc | aatccacccc | catctcccta | aagctagaac actgccaact | |
| 551 | gatctgttgt | ataggtcctt | tagaaacaca | taattaggct gggcgtggcg | |
| 601 | gatcacaagg | tcaggagatt | gaaaccatcc | tggctaacac ggtgaaaccc | |
| 651 | cgtctctact | aaaaatacaa | aaattagct | gggcgtggtg gcgggcacct | |
| 701 | gtagtcccag | ctactctgga | ggctgaggca | ggagaatggc atgaacccag | |
| 751 | taggcagagc | ttgcagcaag | ccgagatcgc | gccactacac tccagcctgg | |
| 801 | acgacagagt | gagactccat | ctcaaaaaaa | aaaaaaaaaa aacaaacaca | |
| 851 | taattaacac | ttaaggttgg | gtgctgccaa | ttctttgtga aaatccaaat | |
| 901 | attattaagg | aaacagggag | atgccactac | ctcttgattt tccatctaaa | |
| 951 | aacatacatg | tttatgcaaa | caaatctttc | catattcata gtgactttc | |
| 1001 | aagtatttga | gtctaaagat | tttcatctca | cattttata ccgtttaaat | |
| 1051 | tgttcacaat | tattacatac | acgtcagcca | tcaactaaag ttgtacttta | |
| 1101 | aaaatttact | acaatatata | cactgctaat | atttgtactt actcttttt | |
| 1151 | tctctagagt | ggaggtataa | ttgtgtgata | cttcagaaat acagataaat | |
| 1201 | gattcaaaaa | gtctcaggga | gaataatgtt | tctttgatcg tgaataactg | |
| 1251 | attagtaatt | cttgcctata | ttttcctgag | agcatatgac aaatgtttct | |
| 1301 | aaggtaacaa | gatgagaaca | gataaagact | gtgtggtctt ttggatttgg | |
| 1351 | agagacatat | tttaattttt | aaatgcagtt | acaaattata atgtattcat | |
| 1401 | atttgtactt | tctgttaaaa | tgcacgattg | caggattatt tagattttgt | |
| 1451 | gtttatgctt | gatgaaaagc tttgttcttg tttttaagtt tgcactcaaa | | | |
| 1501 | ccttaagaaa | taaattcacc | catattatca | aaaaaaatat ttgtcctcgt | |
| 1551 | gtttgttatt | cgatcttgca | gttcactctc | aggaacgcaa gctcagatga | |
| 1601 | cccctaaaat | ggtctctaga | taagttcatg | attgctcaac atcttcaatc | |
| 1651 | ttttgagtat | gggtcacatt | atacctctct | ttatcagcaa gtaaacttta | |
| 1701 | caacaaacat | gtgacatgct | gggacaaggt taaagatcgt tttatccttg | | |
| 1751 | ctgtaaaagc | tgatctgcct gtaGCTGCCA CAGCCTCCAG CGGTGGCTAC | | | |
| 1801 | AGTTGAAACC | CTCACACCAC | GCAGGAAGAG | GTCATCATCA TGTCGGACGA | |
| 1851 | TTTCTTATGG | TTTGAAGGCA | TAGCTTTCCC | TACTATGGGT TTCAGATCCG | |
| 1901 | AAACCTTAAG | AAAAGTACGT | GATGAGTTCG | TGATAAGGGA TGAAGATGTA | |
| 1951 | ATAATATTGA | CTTACCCCAA | ATCAGgtaag | gaggcagaat cgtgaactga | |
| 2001 | gaaaggctgt | ggttgtgttc | ctgtccattc | agtgcatgat tggagttctt | |
| 2051 | cctttatgtc agacagtgta caatgcttta aggggaagag aggaatgcct | | | | |
| 2101 | aataccattg | acaatcagag | aaaaggattt | agtcaggaaa ttacacagta | |
| 2151 | ggatgagtgt | tcagagggt | aatctaaggt | attaggagaa tccacaggag | |
| 2201 | tgaatcccaa | ggcaaat. . . . . . . INTRON 1 . . . . . . . . . . | | | |
| 2218+ | | | | | |
| 1 | atgtccggct gagatggtac attttatata | | ttttttcct tcttttcca | | U13057 |
| 51 | gGAACAAACT | GGTTGGCTGA | GATTCTCTGC | CTGATGCACT CCAAGGGGGA | EXON 2 |
| 101 | TGCCAAGTGG | ATCCAATCTG | TGCCCATCTG | GGAGCGATCA CCCTGGGTAG | |
| 151 | AGAGTGAGAT | TGGGTATACA | GCACTCAGTG | AAACGGAGAG TCCACGTTTA | |
| 201 | TTCTCCTCCC | ACCTCCCCAT | CCAGTTATTC | CCCAAGTCTT TCTTCAGTTC | |
| 251 | CAAGGCCAAG | gtcagtgcat | aatggttaag | acgtgtttga tcagtgcctt | |
| 301 | tcaaacactg | atatgcctat | aagtcatctg | gagatcttgc tgaaatgcat | |
| 351 | tctccttcaa caggtctgtg ttgttgagac | | ctgagattcc gtattagg. . | | |
|  | . . . . . . . . . . . . . . . INTRON 2 . . . . . . . . . . . . . | | | | |
| 2616+ | | | | | |

Figure 1

```
    1  tgcttccttc ttccattgat atattcctag tgcagtgact acttcatagg  U13058
   51  cacgtcaaat ttgattagtg agtgcagtaa gtaatttgtt aaaagaatcc  Exon 3
  101  attgatatta ttaggcatta tccaggaatt ggcttttct ccattttgt
  151  gaagatcaaa aagagtgagg attactgta ttgatttttc attctcccgt
  201  ttttccattt aagGTGATTT ATCTCATGAG AAATCCCAGA GATGTTTTGG
  251  TGTCTGGTTA TTTTTTCTGG AAAAACATGA AGTTTATTAA GAAACCAAAG
  301  TCATGGGAAG AATATTTTGA ATGGTTTTGT CAAGGAACTG gtgagtgttt
  351  cacaaaatat gggggtgctt ggagtcttct agccgacctc ttttgacacc
  401  cagcctcaca tctctacatc tcaccaaccc atgggttgaa aggctccacc
  451  acccctggag gccaaacctg ctaagttcgc ttactctccc gcatagcagc
  501  agaactctag ccgg. . . . . . INTRON 3 . . . . . . . . . . .
3130+
    1  acatctgtta tatactgtaa atatatacca tttgttggtc cccttcgacc  U13059
   51  aagtttcatt caagttttat ttgtcaatca tacgttaaca agccggtggg  Exon 4
  101  gggatgaaca taatagactg gatgcctgct ctcataaaat ttgtaaccta
  151  tcactttttc tgccaccca tgcagTGCTA TATGGGTCAT GGTTTGACCA
  201  CATTCATGGC TGGATGCCCA TGAGAGAGGA GAAAAACTTC CTGTTACTGA
  251  GTTATGAGGA GCTGAAACAG gtaatcccat catttttaga gtcagtgcac
  301  accctctcac caccatcctt actttcctta aattccctcc atcccgctgt
  351  gtcttcattc caccctctca gttaaagtgg a. . . INTRON 4 . . . . .
3511+
    1  gggattacac ggtgaaccac cacgcccagc cttgtctttc tctttcgtat  U13060
   51  cctctctctt gattttttct tttagGACA CAGGAAGAAC CATAGAGAAG  EXON 5
  101  ATCTGTCAAT TCCTGGGAAA GACGTTAGAA CCCGAAGAAC TGAACTTAAT
  151  TCTCAAGAAC AGCTCCTTTC AGAGCATGAA AGAAAACAAG ATGTCCAATT
  201  ATTCCCTCCT GAGTGTTGAT TATGTAGTGG ACAAAGCACA ACTTCTGAGA
  251  AAAGgtaaaa gaaaatcctc tggtttccaa atataccaga atacacggca
  301  tgcatgccta tggtcacaac tgggcgctaa cagttgagat gaaagagtgc
  351  tttttttttt tttttttttt ttccgagatg aagtcttgct ctatcaccca
  401  ggctggagtg cagtgg. . . . . . . . INTRON 5 . . . . . . . .
3927+
    1  ctgctatgtt agctacaatg tccatgtcag gtgcctggtg gagacaggtc  U13061
   51  aaggagatgt gtggtctgac ctgagtttct gcttcttgtt tccagGTGTA  Exon 6
  101  TCTGGGGACT GGAAAAATCA CTTCACAGTG GCCCAAGCTG AAGACTTTGA
  151  TAAATTGTTC CAAGAGAAGA TGGCAGATCT TCCTCGAGAG CTGTTCCCAT
  201  GGGAATAACG TCCAAAACAC TCTGGATCTT ATATGGAGAA TGACATTGAT
  251  TCTCCTGTCC TTGTACATGT ACCTGACTGG GGTCATTGTG TAAGACTTAT
  301  TATTTTATCC TGAAACCTTA AATATCAAAC CTCTGCATCT CTGATCCCTT
  351  CCTTGTTAAA AGTTACCACG GTTGGCCAGG CGCGGTGGTT CATGCCTGTA
  401  ATCCCAGCAC TATGGGAGGC CGAGACGGGC GGATCACGAG GTCAGGAGAC
  451  TGAGACCATC CTGGCTAACA CGGTGAAACC CCATCTCTAC TAAAAATACA
  501  AAAACCAAAA AAAATTAGCC AGGCGCATTG GCTCAGTGTC TGTAATCCCA
  551  GCACTTTGGG AGGTCGGGGG GGTGGGGGAG GATCACGGGG TCAGGAGATC
  601  GAGACCATCC TGGCCAACAT GATGAAACCC TATCTCTACT AAAAATACAA
  651  AAATTAGCCG GCATGGTGG TGCACGCCTA TAGTCCCAGC TACTCGGGAG
  701  GCTGAGGTAG GAGAATCGTT TGAACTCAGG AGGCAGAGGT TGCAATGAGC
  751  CAAGATCGCG CCACTGCACT CCAGCCTGGG TGACAGAGCG AGACCGTCTC
  801  AAAAAGAAAG AAGTGACTAG GGTTCAGAGA ACCAGGGTTC AAAGCCCAGG
  851  GATGCAAAGG TTGCAGTGAG TTGAGTCATG GGATCCCAGA CTTTTTTAAA
  901  TGTTTGCAAT GTTTCCCGTT TACAGAATGC TACAAGAATA ATGTACGTAC
  951  TACCTAAAAG GATGTCTAAA TGTTTGTTAA TAAAAATAAG AAATAGCTAC
 1001  AGTGACAGAT TTTAGAGCAA AAATTAGTAA TAAAAATAAG AAATAAAATT
 1051  ACAGGAGCAA TTaaggttcc atttcttttc atcacatgta tctccacaat
 1101  ttattattgc tctgatctta aggagtgtaa tttgcaatct aatttttatcc
 1151  tcttactctg tgttgttaaa ccatatacaa taaacggtgt ttatggaggc
 1201  ttctaaaact ttcataaggc caggtgcggt gg   (SEQ ID NO:1)
```

Figure 1, continued

```
cgcaggaaga ggtcatcatc atgtcggacg atttcttatg gtttgaaggc atagctttcc    60
ctactatggg tttcagatcc gaaaccttaa gaaaagtacg tgatgagttc gtgataaggg   120
atgaagatgt aataatattg acttaccca aatcaggaac aaactgttg gctgagattc   180
tctgcctgat gcactccaag ggggatgcca agtggatcca atctgtgccc atctgggagc   240
gatcaccctg ggtagagagt gagattgggt atacagcact cagtgaaacg gagagtccac   300
gtttattctc ctcccacctc cccatccagt tattcccca gtcttcttc agttccaagg   360
ccaagtgat ttatctcatg agaaatccca gagatgttt ggtgtctggt tattttttct   420
ggaaaaacat gaagtttatt aagaaaccaa agtcatggga agaatatttt gaatggtttt   480
gtcaaggaac tgtgctatat gggtcatggt ttgaccacat tcatgctgg atgcccatga   540
gagaggagaa aaacttcctg ttactgagtt atgaggagct gaaacaggac acaggaagaa   600
ccatagagaa gatctgtcaa ttcctggaa agacgttaga acccgaagaa ctgaacttaa   660
ttctcaagaa cagctccttt cagagcatga aagaaaacaa gatgtccaat tattccctcc   720
tgagtgttga ttatgtagtg gacaaagcac aacttctgag aaaagtgta tctgggact   780
ggaaaatca cttcacagtg gcccaagctg aagactttga gggaataacg tccaaaacac   840
tggcagatct tcctcgagag ctgttcccat ctgttccgtc ttgtacatgt acctgactgg   900
atatggagaa tgacattgat tattttatcc tgaaacctta aatatcaaac ctctgcatct   960
taagacttat agttaccacg gttggccagg cgcggtggtt catgcctgta atcccagcac  1020
cctttgttaaa agttaccacg ggatcacgag gtcaggagac tgagaccatc ctggctaaca  1080
tatggaggc cgagacgggc ggatcacgag gtcaggagac tgagaccatc ctggctaaca  1140
cggtgaaacc ccatctctac taaaaataca aaaaattagc caaaattagcc agggcattgg  1200
ctcatgtctg taatcccagc actttgggag gtcggggggg tggggagga tcacgggtc  1260
aggagatcga gaccatcctg gccaacatga gccaaccta tgaaaccta tctctactaa aaatacaaaa  1320
attagccggg catggtggtg cacgcctata gtccagcta gtccagcta tgaggtagga  1380
gaatcgtttg aactcaggag gcagaggttg caatgagcca agatcgcgcc actgcactcc  1440
agcctgggtg acagagcgag accgtctcaa aaagaaagaa gtgactaggt tcagagaacc  1500
agggttcaaa gcccagggat gcaaaggttg ccaaggttg cagtgagttg agtcatggga  1560
tttaaatgt ttgcaatgtt tccgtttac agaatgctac aagaatgaaa tcccagactt  1620
ctaaaggat gtctaaatgt ttgttaataa aataagaaa tagctacagt tacgtactac  1680
agagcaaaaa ttagtaataa aataagaaa taaaatta (SEQ ID NO:2)
```

Figure 2A

MSDDFLWFEGIAFPTMGFRSETLRKVRDEFVIRDEDVIILTYPKSGTNWLAEILCLMHSKGDAKWIQ
SVPIWERSPWVESEIGYTALSESESPRLFSSHLPIQLFPKSFFSSKAKVIYLMRNPRDVLVSGYFFW
KNMKFIKKPKSWEEYFEWFCQGTVLYGSWFDHIHGWMPMREEKNFLLLSYEELKQDTGRTIEKIC
QFLGKTLEPEELNLILKNSSFQSMKENKMSNYSLLSVDYVVDKAQLLRKGVSGDWKNHFTVAQAE
DFDKLFQEKMADLPRELFPWE (SEQ ID NO:3)

SEQUENCE LISTING

<160> NUMBER OF SEQ ID NOS: 22

<210> SEQ ID NO 1
<211> LENGTH: 1232
<212> TYPE: DNA
<213> ORGANISM: Homo Sapiens

<400> SEQUENCE: 1

```
ctgctatgtt agctacaatg tccatgtcag gtgcctggtg gagacaggtc aaggagatgt      60
gtggtctgac ctgagtttct gcttcttgtt tccaggtgta tctggggact ggaaaaatca     120
cttcacagtg gcccaagctg aagactttga taaattgttc caagagaaga tggcagatct     180
tcctcgagag ctgttcccat gggaataacg tccaaaacac tctggatctt atatggagaa     240
tgacattgat tctcctgtcc ttgtacatgt acctgactgg ggtcattgtg taagacttat     300
tattttatcc tgaaaccttta aatatcaaac ctctgcatct ctgatccctt ccttgttaaa     360
agttaccacg gttggccagg cgcggtggtt catgcctgta atcccagcac tatgggaggc     420
cgagacgggc ggatcacgag gtcaggagac tgagaccatc ctggctaaca cggtgaaacc     480
ccatctctac taaaaataca aaaccaaaa aaaattagcc aggcgcattg gctcagtgtc     540
tgtaatccca gcactttggg aggtcggggg ggtgggggag gatcacgggg tcaggagatc     600
gagaccatcc tggccaacat gatgaaaccc tatctctact aaaaatacaa aaattagccg     660
ggcatggtgg tgcacgccta tagtcccagc tactcgggag gctgaggtag gagaatcgtt     720
tgaactcagg aggcagaggt tgcaatgagc caagatcgcg ccactgcact ccagcctggg     780
tgacagagcg agaccgtctc aaaaagaaag aagtgactag ggttcagaga accagggttc     840
aaagcccagg gatgcaaagg ttgcagtgag ttgagtcatg ggatcccaga cttttttaaa     900
tgtttgcaat gtttcccgtt tacagaatgc tacaagaata atgtacgtac tacctaaaag     960
gatgtctaaa tgtttgttaa taaaaataag aaatagctac agtgacagat tttagagcaa    1020
aaattagtaa taaaaataag aaataaaatt acaggagcaa ttaaggttcc atttcttttc    1080
atcacatgta tctccacaat ttattattgc tctgatctta aggagtgtaa tttgcaatct    1140 aatttttatcc tcttactctg tgttgttaaa ccatatacaa taaacggtgt ttatggaggc    1200
ttctaaaact ttcataaggc caggtgcggt gg                                  1232
```

<210> SEQ ID NO 2
<211> LENGTH: 1718
<212> TYPE: DNA
<213> ORGANISM: Hiomo Sapiens

<400> SEQUENCE: 2

| | | | | | |
|---|---|---|---|---|---|
| cgcaggaaga | ggtcatcatc | atgtcggacg | atttcttatg | gtttgaaggc | atagctttcc | 60 |
| ctactatggg | tttcagatcc | gaaaccttaa | gaaaagtacg | tgatgagttc | gtgataaggg | 120 |
| atgaagatgt | aataatattg | acttacccca | atcaggaac | aaactggttg | gctgagattc | 180 |
| tctgcctgat | gcactccaag | ggggatgcca | agtggatcca | atctgtgccc | atctgggagc | 240 |
| gatcaccctg | ggtagagagt | gagattgggt | atacagcact | cagtgaaacg | gagagtccac | 300 |
| gtttattctc | ctcccacctc | cccatccagt | tattccccaa | gtctttcttc | agttccaagg | 360 |
| ccaaggtgat | ttatctcatg | agaaatccca | gagatgtttt | ggtgtctggt | tattttttct | 420 |
| ggaaaaacat | gaagtttatt | aagaaaccaa | agtcatggga | agaatatttt | gaatggtttt | 480 |
| gtcaaggaac | tgtgctatat | gggtcatggt | ttgaccacat | tcatggctgg | atgcccatga | 540 |
| gagaggagaa | aaacttcctg | ttactgagtt | atgaggagct | gaaacaggac | acaggaagaa | 600 |
| ccatagagaa | gatctgtcaa | ttcctgggaa | agacgttaga | acccgaagaa | ctgaacttaa | 660 |
| ttctcaagaa | cagctccttt | cagagcatga | agaaaacaa | gatgtccaat | tattccctcc | 720 |
| tgagtgttga | ttatgtagtg | gacaaagcac | aacttctgag | aaaaggtgta | tctggggact | 780 |
| ggaaaaatca | cttcacagtg | gcccaagctg | aagactttga | taaattgttc | caagagaaga | 840 |
| tggcagatct | tcctcgagag | ctgttcccat | gggaataacg | tccaaaacac | tctggatctt | 900 |
| atatggagaa | tgacattgat | tctcctgtcc | ttgtacatgt | acctgactgg | ggtcattgtg | 960 |
| taagacttat | tattttatcc | tgaaaccta | aatatcaaac | ctctgcatct | ctgatccctt | 1020 |
| ccttgttaaa | agttaccacg | gttggccagg | cgcggtggtt | catgcctgta | atcccagcac | 1080 |
| tatgggaggc | cgagacgggc | ggatcacgag | gtcaggagac | tgagaccatc | ctggctaaca | 1140 |
| cggtgaaacc | ccatctctac | taaaaataca | aaaacaaaa | aaattagcc | agggcattgg | 1200 |
| ctcatgtctg | taatcccagc | actttgggag | gtcgggggg | tggggagga | tcacgggtc | 1260 |
| aggagatcga | gaccatcctg | gccaacatga | tgaaaccta | tctctactaa | aaatacaaaa | 1320 |
| attagccggg | catggtggtg | cacgcctata | gtcccagcta | ctcgggggc | tgaggtagga | 1380 |
| gaatcgtttg | aactcaggag | gcagaggttg | caatgagcca | agatcgcgcc | actgcactcc | 1440 |
| agcctgggtg | acagagcgag | accgtctcaa | aaagaaagaa | gtgactaggt | tcagagaacc | 1500 |
| agggttcaaa | gcccagggat | gcaaaggttg | cagtgagttg | agtcatggga | tcccagactt | 1560 |
| ttttaaatgt | ttgcaatgtt | tcccgtttac | agaatgctac | aagaataatg | tacgtactac | 1620 |
| ctaaaaggat | gtctaaatgt | ttgttaataa | aaataagaaa | tagctacagt | gacagatttt | 1680 |
| agagcaaaaa | ttagtaataa | aaataagaaa | taaaatta | | | 1718 |

<210> SEQ ID NO 3
<211> LENGTH: 285
<212> TYPE: PRT
<213> ORGANISM: Homo Sapiens

<400> SEQUENCE: 3

Met Ser Asp Asp Phe Leu Trp Phe Glu Gly Ile Ala Phe Pro Thr Met
 1               5                  10                  15

Gly Phe Arg Ser Glu Thr Leu Arg Lys Val Arg Asp Glu Phe Val Ile
            20                  25                  30

```
Arg Asp Glu Asp Val Ile Ile Leu Thr Tyr Pro Lys Ser Gly Thr Asn
        35                  40                  45

Trp Leu Ala Glu Ile Leu Cys Leu Met His Ser Lys Gly Asp Ala Lys
    50                  55                  60

Trp Ile Gln Ser Val Pro Ile Trp Glu Arg Ser Pro Trp Val Glu Ser
65                  70                  75                  80

Glu Ile Gly Tyr Thr Ala Leu Ser Glu Ser Glu Ser Pro Arg Leu Phe
                85                  90                  95

Ser Ser His Leu Pro Ile Gln Leu Phe Pro Lys Ser Phe Phe Ser Ser
                100                 105                 110

Lys Ala Lys Val Ile Tyr Leu Met Arg Asn Pro Arg Asp Val Leu Val
            115                 120                 125

Ser Gly Tyr Phe Phe Trp Lys Asn Met Lys Phe Ile Lys Lys Pro Lys
        130                 135                 140

Ser Trp Glu Glu Tyr Phe Glu Trp Phe Cys Gln Gly Thr Val Leu Tyr
145                 150                 155                 160

Gly Ser Trp Phe Asp His Ile His Gly Trp Met Pro Met Arg Glu Glu
                165                 170                 175

Lys Asn Phe Leu Leu Leu Ser Tyr Glu Glu Leu Lys Gln Asp Thr Gly
                180                 185                 190

Arg Thr Ile Glu Lys Ile Cys Gln Phe Leu Gly Lys Thr Leu Glu Pro
            195                 200                 205

Glu Glu Leu Asn Leu Ile Leu Lys Asn Ser Ser Phe Gln Ser Met Lys
        210                 215                 220

Glu Asn Lys Met Ser Asn Tyr Ser Leu Leu Ser Val Asp Tyr Val Val
225                 230                 235                 240

Asp Lys Ala Gln Leu Leu Arg Lys Gly Val Ser Gly Asp Trp Lys Asn
                245                 250                 255

His Phe Thr Val Ala Gln Ala Glu Asp Phe Asp Lys Leu Phe Gln Glu
                260                 265                 270

Lys Met Ala Asp Leu Pro Arg Glu Leu Phe Pro Trp Glu
            275                 280                 285

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
tgtaaaacga cggccagtgc tttgttcttg tttttaagtt tgcac          45

<210> SEQ ID NO 5
<211> LENGTH: 45
<212> TYPE: DNA
<213> ORGANISM: Artificial Sequence
<220> FEATURE:
<223> OTHER INFORMATION: Primer

<400> SEQUENCE: 5
caggaaacag ctatgaccca ccgctggagg ctgtggcagc tacag          45

<210> SEQ ID NO 6
<211> LENGTH: 44
<212> TYPE: DNA
<213> ORGANISM: Artificial Sequence
<220> FEATURE:
<223> OTHER INFORMATION: Primer
```

```
<400> SEQUENCE: 6
tgtaaaacga cggccagtgg gacaaggtta aagatcgttt tatc          44

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
caggaaacag ctatgaccaa gcattgtaca ctgtctgac               39

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
tgtaaaacga cggccagtat gtccggctga gatggtaca               39

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
caggaaacag ctatgaccaa cacagacctg ttgaaggag               39

<210> SEQ ID NO 10
<211> LENGTH: 42
<212> TYPE: DNA
<213> ORGANISM: Artificial Sequence
<220> FEATURE:
<223> OTHER INFORMATION: Primer

<400> SEQUENCE: 10
tgtaaaacga cggccagtat tgatattatt aggcattatc ca           42

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
caggaaacag ctatgaccag gtttggcctc cagggtgg                39

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
tgtaaaacga cggccagtac atctgtttata tactgtaaa              39
```

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
caggaaacag ctatgaccgg tggaatgaag acacag                                36

<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
tgtaaaacga cggccagtgg gattacacgg tgaaccacc                             39

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15
caggaaacag ctatgaccaa gctctctttc atctcaact                             39

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
tgtaaaacga cggccagtct gctatgttag ctacaatgtc ca                         42

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
caggaaacag ctatgacctt ttaacaagga agggatcag                             39

<210> SEQ ID NO 18
<211> LENGTH: 2217
<212> TYPE: DNA
<213> ORGANISM: Homo Sapiens

<400> SEQUENCE: 18
gggttcatgc cattctcctg cctcagcctc ctgagtagct gggactacag gcacccgcca      60
ccacgcccgg ctaatttttt gtatttttag tagagacggg gtttcaccgt gttagccagg     120
atggtctcga tctcctgacc tcgtgatccg cccgcctcgg cctcccaaag tgctgggatt     180
acaggcgtga gcaccacacc gtgcccagac caagaatgaa ggttttttgta aagatttctg    240 ttcagtgttt tgcaaggtaa aattctaggc acgttttccc tgaagttatg tgtatgtgag    300
tattctcatt cttcccaact tgcctttgaa gagtgaaaaa acattattat caagtagact    360

```
tctattcagc ttttgctcct gccctgctgt ttatcccctta agaatgagtt tcttggactt       420
tcccaatatg tgattttttt ttcccattta gaatggtgat tttaaatgtg tgagtgcatg       480
cattatctta tctcagatat ttgcacccccc aatccacccc catctcccta aagctagaac      540
actgccaact gatctgttgt ataggtcctt tagaaacaca taattaggct gggcgtggcg       600
gatcacaagg tcaggagatt gaaaccatcc tggctaacac ggtgaaaccc cgtctctact       660
aaaaatacaa aaaattagct gggcgtggtg gcgggcacct gtagtcccag ctactctgga       720
ggctgaggca ggagaatggc atgaacccag taggcagagc ttgcagcaag ccgagatcgc       780
gccactacac tccagcctgg acgacagagt gagactccat ctcaaaaaaa aaaaaaaaaa       840
aacaaacaca taattaacac ttaaggttgg gtgctgccaa ttctttgtga aaatccaaat       900
attattaagg aaacagggag atgccactac ctcttgattt tccatctaaa aacatacatg       960
tttatgcaaa caaatctttc catattcata gtgacttttc aagtatttga gtctaaagat      1020
tttcatctca catttttata ccgtttaaat tgttcacaat tattacatac acgtcagcca      1080
tcaactaaag ttgtacttta aaaatttact acaatatata cactgctaat atttgtactt      1140
actctttttt tctctagagt ggaggtataa ttgtgtgata cttcagaaat acagataaat      1200
gattcaaaaa gtctcaggga gaataatgtt tctttgatcg tgaataactg attagtaatt      1260
cttgcctata ttttcctgag agcatatgac aaatgtttct aaggtaacaa gatgagaaca      1320
gataaagact gtgtggtctt tggatttgg agagacatat tttaattttt aaatgcagtt       1380
acaaattata atgtattcat atttgtactt tctgttaaaa tgcacgattg caggattatt      1440
tagattttgt gtttatgctt gatgaaaagc tttgttcttg tttttaagtt tgcactcaaa      1500
ccttaagaaa taaattcacc catattatca aaaaaaatat ttgtcctcgt gtttgttatt      1560
cgatcttgca gttcactctc aggaacgcaa gctcagatga cccctaaaat ggtctctaga      1620
taagttcatg attgctcaac atcttcaatc ttttgagtat gggtcacatt atacctctct      1680
ttatcagcaa gtaaacttta caacaaacat gtgacatgct gggacaaggt taaagatcgt      1740
tttatccttg ctgtaaaagc tgatctgcct gtagctgcca cagcctccag cggtggctac      1800
agttgaaacc ctcacaccac gcaggaagag gtcatcatca tgtcggacga tttcttatgg      1860
tttgaaggca tagcttttccc tactatgggt ttcagatccg aaaccttaag aaaagtacgt      1920
gatgagttcg tgataaggga tgaagatgta ataatattga cttaccccaa atcaggtaag      1980
gaggcagaat cgtgaactga gaaaggctgt ggttgtgttc ctgtccattc agtgcatgat      2040
tggagttctt cctttatgtc agacagtgta caatgcttta aggggaagag aggaatgcct      2100
aataccattg acaatcagag aaaaggattt agtcaggaaa ttacacagta ggatgagtgt      2160
tcagaggggt aatctaaggt attaggagaa tccacaggag tgaatcccaa ggcaaat        2217
```

<210> SEQ ID NO 19  
<211> LENGTH: 398  
<212> TYPE: DNA  
<213> ORGANISM: Homo Sapiens

<400> SEQUENCE: 19

```
atgtccggct gagatggtac attttatata ttttttttcct tcttttttcca ggaacaaact       60 ggttggctga gattctctgc ctgatgcact ccaaggggga tgccaagtgg atccaatctg      120
tgcccatctg ggagcgatca ccctgggtag agagtgagat tgggtataca gcactcagtg      180
aaacggagag tccacgtttta ttctcctccc acctccccat ccagttattc cccaagtctt      240
tcttcagttc caaggccaag gtcagtgcat aatggttaag acgtgtttga tcagtgcctt      300
```

-continued

| | |
|---|---|
| tcaaacactg atatgcctat aagtcatctg gagatcttgc tgaaatgcat tctccttcaa | 360 |
| caggtctgtg ttgttgagac ctgagattcc gtattagg | 398 |

<210> SEQ ID NO 20
<211> LENGTH: 514
<212> TYPE: DNA
<213> ORGANISM: Homo Sapiens

<400> SEQUENCE: 20

| | |
|---|---|
| tgcttccttc ttccattgat atattcctag tgcagtgact acttcatagg cacgtcaaat | 60 |
| ttgattagtg agtgcagtaa gtaatttgtt aaaagaatcc attgatatta ttaggcatta | 120 |
| tccaggaatt ggcttttttct ccattttttgt gaagatcaaa aagagtgagg attgactgta | 180 |
| ttgatttttc attctcccgt ttttccattt aaggtgattt atctcatgag aaatcccaga | 240 |
| gatgttttgg tgtctggtta ttttttctgg aaaaacatga agtttattaa gaaaccaaag | 300 |
| tcatgggaag aatattttga atggttttgt caaggaactg gtgagtgttt cacaaaatat | 360 |
| gggggtgctt ggagtcttct agccgacctc ttttgacacc cagcctcaca tctctacatc | 420 |
| tcaccaaccc atgggttgaa aggctccacc acccctggag gccaaacctg ctaagttcgc | 480 |
| ttactctccc gcatagcagc agaactctag ccgg | 514 |

<210> SEQ ID NO 21
<211> LENGTH: 381
<212> TYPE: DNA
<213> ORGANISM: Homo Sapiens

<400> SEQUENCE: 21

| | |
|---|---|
| acatctgtta tatactgtaa atatatacca tttgttggtc cccttcgacc aagtttcatt | 60 |
| caagttttat ttgtcaatca tacgttaaca agccggtggg gggatgaaca taatagactg | 120 |
| gatgcctgct ctcataaaat ttgtaaccta tcactttttc tgccaccca tgcagtgcta | 180 |
| tatgggtcat ggtttgacca cattcatggc tggatgccca tgagagagga gaaaaacttc | 240 |
| ctgttactga gttatgagga gctgaaacag gtaatcccat cattttttaga gtcagtgcac | 300 |
| accctctcac caccatcctt actttcctta aattccctcc atcccgctgt gtcttcattc | 360 |
| caccctctca gttaaagtgg a | 381 |

<210> SEQ ID NO 22
<211> LENGTH: 415
<212> TYPE: DNA
<213> ORGANISM: Homo Sapiens

<400> SEQUENCE: 22

| | |
|---|---|
| gggattacac ggtgaaccac cacgcccagc cttgtctttc tctttcgtat cctctctctt | 60 |
| gattttttctt ttttaggaca caggaagaac catagagaag atctgtcaat tcctgggaaa | 120 |
| gacgttagaa cccgagaact gaacttaatt ctcaagaaca gctcctttca gagcatgaaa | 180 |
| gaaaacaaga tgtccaatta ttccctcctg agtgttgatt atgtagtgga caaagcacaa | 240 |
| cttctgagaa aaggtaaaag aaaatcctct ggtttccaaa tataccagaa tacacggcat | 300 |
| gcatgcctat ggtcacaact gggcgctaac agttgagatg aaagagtgct tttttttttt | 360 |
| tttttttttt tccgagatga agtcttgctc tatcacccag gctggagtgc agtgg | 415 |

SULFOTRANSFERASE SULT2A1 SEQUENCE VARIANTS

CROSS REFERENCE TO RELATED APPLICATIONS

This application claims priority from U.S. Provisional Application Ser. No. 60/300,165, filed on Jun. 22, 2001.

STATEMENT AS TO FEDERALLY SPONSORED RESEARCH

Funding for the work described herein was provided in part by the federal government (NIH grants RO1 GM28157, RO1GM35720, and U01 GM61388), which may have certain rights in the invention.

TECHNICAL FIELD

The invention relates to sulfotransferase nucleic acid and amino acid sequence variants.

BACKGROUND

Sulfate conjugation is an important pathway in the biotransformation of many neurotransmitters, hormones, drugs and other xenobiotics, and is catalyzed by cytosolic sulfotransferase enzymes designated "SULT." SULT enzymes are encoded by a gene superfamily, which, in mammals, is divided into two families, SULT1 or phenol SULTs and SULT2 or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) SULTs. SULT2 subfamilies include two hydroxysteroid SULTs, 2A1 and 2B1.

Members of the SULT2A subfamily, including SULT2A1, catalyze the sulfate conjugation of hydroxysteroids, such as dehydroepiandrosterone (DHEA). Human SULT2A1 is expressed in the liver, small intestine, and adrenal cortex.

SUMMARY

The invention is based on the discovery of sequence variants that occur in both coding and non-coding regions of SULT2A1 nucleic acids. Certain SULT2A1 nucleotide sequence variants encode SULT2A1 enzymes that are associated with individual differences in enzymatic activity. Other SULT2A1 nucleotide sequence variants in non-coding regions of the SULT2A1 nucleic acid may alter regulation of transcription and/or splicing of the SULT2A1 nucleic acid. Discovery of these sequence variants allows individual differences in the sulfate conjugation of drugs and other xenobiotics in humans to be assessed such that particular treatment regimens can be tailored to an individual based on the presence or absence of one or more sequence variants. Identification of SULT2A1 nucleotide sequence variants also allows predisposition to hormone dependent diseases or cancer to be assessed in individuals.

In one aspect, the invention features an isolated nucleic acid molecule that includes a SULT2A1 nucleic acid sequence, wherein the nucleic acid molecule is at least ten nucleotides in length, and wherein the SULT2A1 nucleic acid sequence includes a nucleotide sequence variant relative to SEQ ID NOS:1, 18, 19, 20, 21, or 22. The nucleotide sequence variant can be within a coding sequence, an intron sequence, a 5' untranslated sequence, or a 3 untranslated sequence, and can be a nucleotide deletion, a nucleotide insertion, or a nucleotide substitution.

The nucleotide sequence variant can be at position 16 relative to the guanine in the splice donor site of intron 1, e.g., a thymine substitution for cytosine. The nucleotide sequence variant can be at position 34 relative to the guanine in the splice donor site of intron 2, e.g., an adenine substitution for guanine. The nucleotide sequence variant can be at positions −94 or −129 relative to the guanine in the splice acceptor site of intron 3, e.g., a guanine substitution for cytosine at position −94 or an adenine substitution for guanine at position −129. The nucleotide sequence variant can be at position 57 relative to the guanine in the splice donor site of intron 3, e.g., a thymine substitution for cytosine.

The nucleotide sequence variant can be at position 67 relative to the guanine in the splice donor site of intron 4, e.g., a thymine substitution for cytosine. The nucleotide sequence variant can be at position −122 relative to the adenine of the SULT2A1 translation initiation codon, e.g., an adenine substitution for guanine.

The nucleotide sequence variant can be at positions 924 or 935 relative to the adenine of the SULT2A1 translation initiation codon, e.g., a cytosine substitution for thymine at position 924 or a thymine substitution for adenine at position 935.

The isolated nucleic acid molecule can include three nucleotide sequence variants. For example, the three nucleotide sequence variants can be at position −122 relative to the adenine of the SULT2A1 translation initiation codon, position 187 relative to the adenine of the SULT2A1 translation initiation codon; and position 781 relative to the adenine of the SULT2A1 translation initiation codon.

The invention also features an isolated nucleic acid encoding a SULT2A1 polypeptide, wherein the polypeptide includes a SULT2A1 amino acid sequence variant relative to the amino acid sequence of SEQ ID NO:3. The amino acid sequence variant can be at one or more residues selected from the group consisting of 63, 227, and 261.

In another aspect, the invention features an isolated SULT2A1 polypeptide, wherein the polypeptide includes a SULT2A1 amino acid sequence variant relative to the amino acid sequence of SEQ ID NO:3. The polypeptide can include a SULT2A1 amino acid sequence variant at one or more residues selected from the group consisting of 63, 227, and 261. For example, the amino acid sequence variant at residue 63 can be a proline; the amino acid sequence variant at residue 227 can be a glutamate; and the amino acid sequence variant at residue 261 can be a threonine. Activity of the polypeptide can be altered relative to a wild type SULT2A1 polypeptide. The polypeptide can contain two amino acid sequence variants (e.g., at positions 63 and 261).

In yet another aspect, the invention features an article of manufacture that includes a substrate, wherein the substrate includes a population of isolated SULT2A1 nucleic acid molecules, each nucleic acid molecule including a SULT2A1 nucleotide sequence variant. The substrate can include a plurality of discrete regions, wherein each region includes a different population of isolated SULT2A1 nucleic acid molecules, and wherein each population of molecules includes a different SULT2A1 nucleotide sequence variant.

The invention also features a method for determining if a mammal is predisposed to a heart condition such as heart attack or stroke, or cancer such as testicular cancer or breast cancer. The method includes obtaining a biological sample from the mammal, and detecting the presence or absence of a SULT2A1 nucleotide sequence variant in the sample, wherein predisposition to a heart condition or cancer is determined based on the presence or absence of the variant. The method further can include detecting the presence or absence of a plurality of SULT2A1 nucleotide sequence variants in the sample to obtain a variant profile of the mammal, and wherein predisposition to the heart condition or cancer is determined based on the variant profile.

The invention also features a method for obtaining a SULT2A1 variant profile. The method includes obtaining a biological sample from a mammal, and detecting the presence or absence of a plurality of SULT2A1 nucleotide sequence variants in the sample to obtain a variant profile of the mammal. The method further can include communicating the profile to a medical or research professional.

In yet another aspect, the invention features an isolated nucleic acid molecule that includes a SULT2A1 nucleic acid sequence, wherein the nucleic acid molecule is at least ten nucleotides in length, and wherein the SULT2A1 nucleic acid sequence has at least 99% sequence identity to a region of SEQ ID NOS:1, 2, 18, 19, 20, 21, or 22, wherein nucleotide −122 relative to the adenine of the SULT2A1 translation initiation codon is an adenine, nucleotide 187 relative to the adenine of the SULT2A1 translation initiation codon is a cytosine, nucleotide 679 relative to the adenine of the SULT2A1 translation initiation codon is a guanine, and nucleotide 781 relative to the adenine of the SULT2A1 translation initiation codon is an adenine. The region of SEQ ID NO:1 can be selected from the group consisting of a) nucleotides −150 to −75 of SEQ ID NO:18 relative to the adenine of the SULT2A1 translation initiation codon; b) nucleotides 150 to 200 of SEQ ID NO:2 relative to the adenine of the SULT2A1 translation initiation codon; c) nucleotides 650 to 700 of SEQ ID NO:2 relative to the adenine of the SULT2A1 translation initiation codon; and d) nucleotides 750 to 800 of SEQ ID NO:2 relative to the adenine of the SULT2A1 translation initiation codon.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is the nucleotide sequence of the reference SULT2A1 (SEQ ID NO:1, and SEQ ID NOS:18–22). Single nucleotide polymorphisms (SNPs) are indicated in underlined italics, exons are in uppercase, introns are in lowercase, coding regions are in boldface, and primer sequences are indicated by thick underlines.

FIG. 2A is an mRNA sequence (SEQ ID NO:2) containing the cDNA sequence of the reference SULT2A1 (nucleotides 21 to 878). FIG. 2B is the amino acid sequence (SEQ ID NO:3) of the reference SULT2A1.

DETAILED DESCRIPTION

Figure 3:
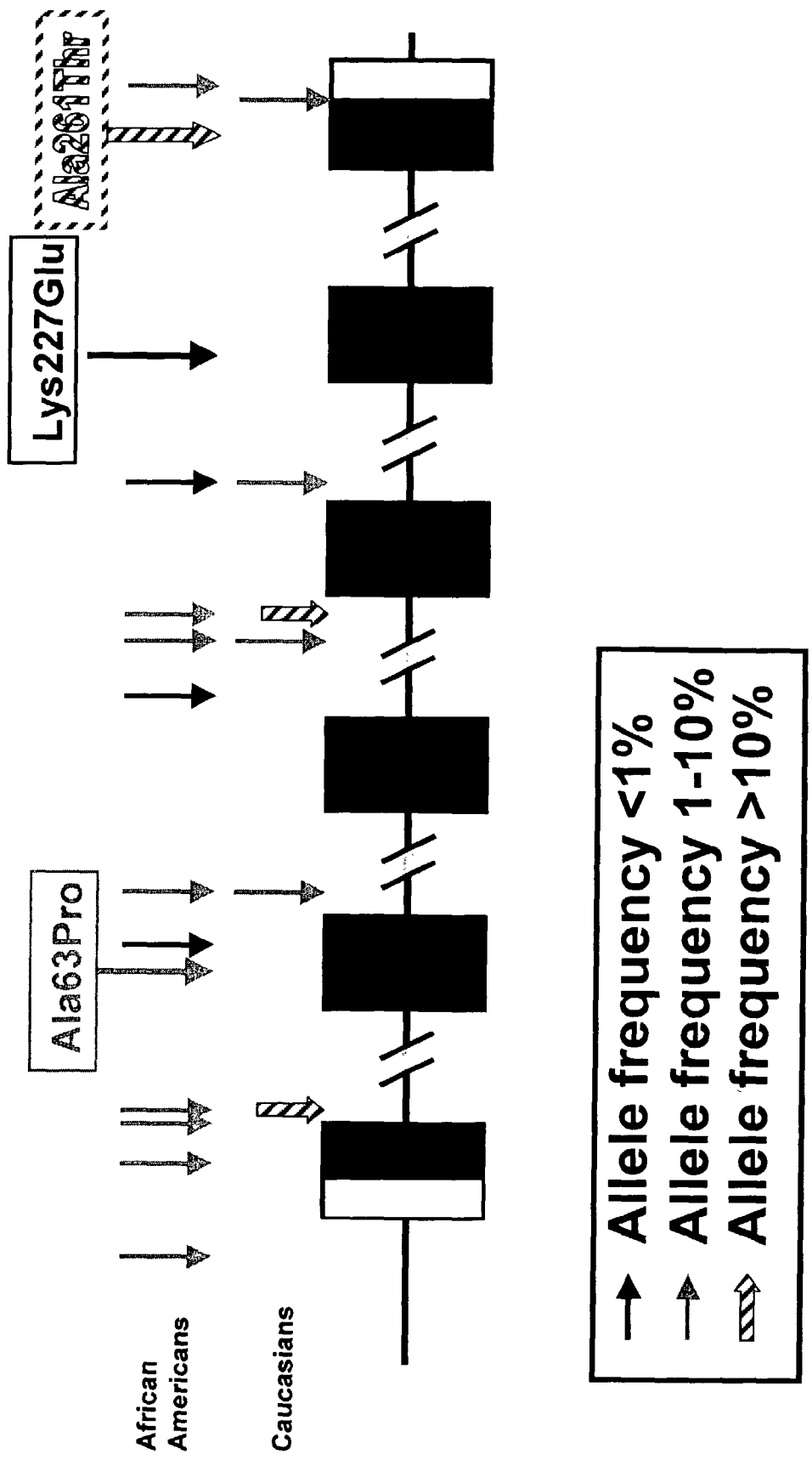
FIG. 3 is a schematic of the location of the non-synonymous polymorphisms within the SULT2A1 amino acid sequence.

The invention features SULT2A1 nucleotide and SULT2A1 amino acid sequence variants. SULT2A1 catalyzes the transfer of inorganic sulfate to hydroxysteroids and uses 3'-phosphoadenosine-5'-phosposulfate (PAPS) as the sulfate donor. Sulfation typically detoxifies compounds as the resulting ionized, organic sulfates are more readily excreted than the unsulfated compounds. Furthermore, functional groups that may interact with biological macromolecules such as nucleic acids or proteins can be masked by the sulfate moiety. SULT2A1 may play a role in the modification of steroids, including, without limitation, DHEA, ethinyl estradiol, minoxidil, androsterone, androstenediol, epiandrosterone, androgens, estrogens (e.g., estrone and 17β, estradiol), testosterone, and pregnenolone.

Genetically based variations in SULT2A1 activity may affect the metabolism of steroid compounds that are used as drugs, as well as structurally related xenobiotics and endogeneous hormones. For example, an individual with decreased SULT2A1 activity might receive greater benefit from an average dose of DHEA compared to an individual with a normal SULT2A1 activity. Conversely, a female using the oral contraceptive ethinyl estradiol with decreased SULT2A1 activity may have higher circulating estrogen concentrations, a known risk factor for vascular conditions such as heart attack or stroke. In addition, detecting sulfotransferase activity can be important in post-menopausal women that are receiving, or are candidates for receiving, hormone replacement therapy. Thus, detecting sulfotransferase nucleic acid and amino acid sequence variants facilitates the prediction of therapeutic efficacy and toxicity of drugs on an individual basis, as well as an individual's ability to biotransform certain hormones.

Nucleic Acid Molecules

The invention features isolated nucleic acids that include a SULT2A1 nucleic acid sequence. The SULT2A1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-SULT2A1 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10–20 (e.g., 11, 12, 13, 14, 15, 16, 17, 18, 19, or 20 nucleotides in length), 20–50, 50–100 or greater than 100 nucleotides in length (e.g., greater than 150, 200, 250, 300, 350, 400, 450, 500, 750, or 1000 nucleotides in length). Nucleic acids of the invention can be in sense or antisense orientation, can be complementary to the SULT2A1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.* (1997) 7(3):187–195; and Hyrup et al. (1996) *Bioorgan. Med. Chem.* 4(1):5–23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in the SULT2A1 reference sequence, and includes variations that occur in coding and non-coding regions, including exons, introns, and untranslated sequences. Nucleotides are referred to herein by the standard one-letter designation (A, C, G, or T). Variations include substitutions of one or more nucleotides, deletions of one or more nucleotides, and insertions of one or more nucleotides. The reference SULT2A1 genomic nucleic acid sequence is provided in FIG. 1 (SEQ ID NO:1, and SEQ ID NOS:18–22) and in GenBank (Accession Nos. U13056, U13057, U13058, U13059, U13060, and U13061). The reference SULT2A1 mRNA including the SULT2A1 cDNA is provided in FIG. 2A (SEQ ID NO:2) and the corresponding amino acid sequence is provided in FIG. 2B (SEQ ID NO:3). Both the mRNA and the amino acid sequences are also found in GenBank (Accession No. U08024). The nucleic acid and amino acid reference sequences also are referred to herein as "wild type". As used herein, "untranslated sequence" includes 5' and 3' flanking regions that are outside of the mRNA as well as 5' and 3' untranslated regions (5'-UTR or 3'-UTR) that are part of the mRNA, but are not translated. Positions of nucleotide sequence variants in 5' untranslated sequences are designated as "–X" relative to the "A" in the initiation codon; positions of nucleotide sequence variants in the coding sequence and 3' untranslated sequence are designated as "+X" or "X" relative to the "A" in the initiation codon. Nucleotide sequence variants that occur in introns are designated as "+X" or "X" relative to "G" in the splice donor site (GT) or as "–X" relative to the "G" in the splice acceptor site (AG).

In some embodiments, a SULT2A1 nucleotide sequence variant encodes a SULT2A1 polypeptide having a SULT2A1 amino acid sequence variant. The term "polypeptide" refers to a chain of at least four amino acid residues (e.g., 4–8, 9–12, 13–15, 16–18, 19–21, 22–100, 100–150, 150–200, 200–300 residues, or a full-length SULT2A1 polypeptide). SULT2A1 polypeptides may or may not have sulfotransferase catalytic activity, or may have activity that is altered relative to the reference SULT2A1 polypeptide. Polypeptides that do not have activity or that have altered activity are useful for diagnostic purposes (e.g., for producing antibodies having specific binding affinity for variant sulfotransferase polypeptides).

Corresponding SULT2A1 polypeptides, irrespective of length, that differ in amino acid sequence are herein referred to as allozymes. For example, a SULT2A1 nucleic acid sequence that includes a cytosine at nucleotide 187 encodes a SULT2A1 polypeptide having a proline at amino acid residue 63. This polypeptide (Ala63Pro) would be considered an allozyme with respect to the reference SULT2A1 polypeptide that contains an alanine at amino acid residue 63. Additional non-limiting examples of SULT2A1 nucleotide sequence variants that encode SULT2A1 amino acid sequence variants include variants at nucleotides 679 and 781. For example, a SULT2A1 nucleic acid molecule can include a guanine at nucleotide 679 and encode a SULT2A1 polypeptide having a glutamate at amino acid residue 227 in place of a lysine residue (Lys227Glu), or an adenine at nucleotide 781 and encode a SULT2A1 polypeptide having a threonine at amino acid 261 in place of an alanine (Ala261Thr).

SULT2A1 allozymes as described above are encoded by a series of sulfotransferase alleles. These alleles represent SULT2A1 nucleic acid sequences containing nucleotide sequence variants, typically multiple nucleotide sequence variants, within coding and non-coding sequences. Representative examples of single nucleotide sequence variants are described above. Table 2 sets out a series of SULT2A1 alleles that encode SULT2A1 amino acid sequence variants. Alleles encoding Ala63Pro and Ala261Thr are commonly observed (allele frequencies>1%). The relatively large number of alleles and allozymes for SULT2A1 indicates the potential complexity of SULT pharmacogenetics. Such complexity emphasizes the need for determining single nucleotide sequence variants, (i.e., single nucleotide polymorphisms, SNPs) as well as complete haplotypes (i.e., the set of alleles on one chromosome or a part of a chromosome) of patients.

Certain SULT2A1 nucleotide sequence variants do not alter the amino acid sequence. Such variants, however, could alter regulation of transcription as well as mRNA stability. SULT2A1 nucleotide sequence variants can occur in intron sequences, for example, within introns 1, 2, 3, or 4. In particular, the nucleotide sequence variant can include a thymine at nucleotide 16 of intron 1. The nucleotide sequence variant can include an adenine at nucleotide 34 of intron 2. Intron 3 variants can include a thymine at nucleotide 57, an adenine at –129, or a guanine at –94. Intron 4 variants include a thymine at 67.

SULT2A1 nucleotide sequence variants that do not change the amino acid sequence also can be within an exon or in 5' or 3' untranslated sequences. For example, the 5' flanking region of SULT2A1 can include a substitution of an adenine at –122. The 3' UTR can contain a cytosine at 924 or a thymine at 935.

In some embodiments, nucleic acid molecules of the invention can have at least 98% e.g., 98.5%, 99.0%, 99.5%, 99.6%, 99.7%, 99.8%, 99.9%, or 100%) sequence identity with a region of SEQ ID NO:1, SEQ ID NO:2, SEQ ID NO:18, SEQ ID NO:19, SEQ ID NO:20, SEQ ID NO:21, or SEQ ID NO:22 that includes one or more variants described herein. The region of SEQ ID NO:1, SEQ BD NO:2, SEQ ID NO:18, SEQ ID NO:19, SEQ ID NO:20, SEQ ID NO:21, or SEQ ID NO:22 is at least 15 nucleotides in length (e.g., 50, 60, 70, 75, 100, 150 or more nucleotides in length). For example, a nucleic acid molecule can have at least 99% identity with a region of SEQ ID NO:1, SEQ ID NO:2, SEQ ID NO:18, SEQ ID NO:19, SEQ ID NO:20, SEQ ID NO:21, or SEQ ID NO:22 containing nucleotides −150 to 800, −150 to −75, −75 to −30, −25 to 50, 55 to 110, 115 to 200, 205 to 275, 300 to 375, 380 to 450, 455 to 525, 530 to 630, 650 to 700, 705 to 745, or 750 to 800 relative to the adenine of the SULT2A1 translation initiation codon, where the nucleotide sequence of SEQ ID NO:1, SEQ ID NO:2, SEQ ID NO:18, SEQ ID NO:19, SEQ ID NO:20, SEQ ID NO:21, or SEQ ID NO:22 includes one or more of the variants described herein. For example, the nucleotide sequence of SEQ ID NO:1, SEQ ID NO:2, SEQ ID NO:18, SEQ ID NO:19, SEQ ID NO:20, SEQ ID NO:21, or SEQ ID NO:22 can have an adenine at nucleotide □122 relative to the adenine of the SULT2A1 translation initiation codon, a cytosine at nucleotide 187 relative to the adenine of the SULT2A1 translation initiation codon, a guanine at nucleotide 679 relative to the adenine of the SULT2A1 translation initiation codon, or an adenine at nucleotide 781 relative to the adenine of the SULT2A1 translation initiation codon, and combinations thereof.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the State University of New York—Old Westbury campus library as well as at Fish & Richardson's web site (www-.fr.com/blast) or the U.S. government's National Center for Biotechnology Information web site (www.ncbi.nlm.nih-.gov/blast/executables). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq -i c:\seq1.txt-j c:\seq2.txt -p blastn -o c:\output.txt -q -1-r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 200 nucleotides from the target sequence aligned with a region of the sequence set forth in SEQ ID NO: 1 where the first and last nucleotides of that 200 nucleotide region are matches, and (3) the number of matches over those 200 aligned nucleotides is 180, then the 1000 nucleotide target sequence contains a length of 200 and a percent identity over that length of 90 (i.e., 180÷200×100=90).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a SULT2A1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, Ed. by Dieffenbach, C. and Dveksler, G., Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis *Genetic Engineering News*, 12(9):1 (1992); Guatelli et al., *Proc. Natl. Acad. Sci. USA*, 87:1874–1878 (1990); and Weiss, *Science*, 254:1292 (1991).

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequence depicted in FIG. 1 or 2A can be mutated using standard techniques including oligonucleotide-directed mutagenesis and site-directed mutagenesis through PCR. See, Short Protocols in Molecular Biology, Chapter 8, Green Publishing Associates and John Wiley & Sons, Edited by Ausubel, F. M et al., 1992. Examples of positions that can be modified are described above.

Vectors and Host Cells

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* ($2^{nd}$ edition), Cold Spring Harbor Laboratory, New York (1989), and reagents for transformation and/or transfection are commercially available (e.g., Lipofectin (Invitrogen/Life Technologies); Fugene (Roche, Indianapolis, Ind.); and SuperFect (Qiagen, Valencia, Calif.)).

SULT2A1 Polypeptides

Isolated SULT2A1 polypeptides of the invention include an amino acid sequence variant relative to the reference SULT2A1 polypeptide (FIG. 2B, SEQ ID NO:3, GenBank Accession No. U08024). The term "isolated" with respect to a SULT2A1 polypeptide refers to a polypeptide that has been separated from cellular components that naturally accompany it. Typically, the polypeptide is isolated when it is at least 60% (e.g., 70%, 80%, 90%, 95%, or 99%), by weight, free from proteins and naturally occurring organic molecules that are naturally associated with it. In general, an isolated polypeptide will yield a single major band on a non-reducing polyacrylamide gel.

SULT2A1 polypeptides of the invention can include variants at one or more of residues 63, 227, and 261. In particular, a proline residue can be substituted at position 63, a glutamate residue at position 227, or a threonine at position 261. In some embodiments, a polypeptide can include a proline at position 63 and a threonine at position 261. Amino acid variants also can be within conserved regions I–IV of the SULT signature sequence. See, Pederson et al., *FEBS Letters* 475:61–64 (2000). For example, the variant can be within region IV or the dimerization motif. As described herein, the Ala261 Thr polymorphism disrupts dimerization of SULT2A1.

Activity of SULT2A1 polypeptides can be altered relative to the reference SULT2A1 polypeptide. As described herein, certain SULT2A1 allozymes have reduced activity (e.g., Ala63Pro, Lys227Glu, and Ala63Pro/Ala261Thr), while other allozymes (Ala261Thr) have activity that is comparable to the reference SULT2A1 polypeptide. Other allozymes can have increased activity relative to the reference SULT2A1 polypeptide. Activity of SULT2A1 polypeptides can be assessed in vitro using a sulfate acceptor substrate such as DHEA and a donor sulfate molecule such as PAPS. In general, recombinant SULT2A1 polypeptides can be incubated at 37° C. with 0.4 µM $^{35}$S-PAPS and 5 µM DHEA in a potassium phosphate buffer (5 mM, pH 6.5). Reactions can be stopped by precipitating PAPS and SULT2A1 polypeptide (e.g., with barium hydroxide, barium acetate, and zinc sulfate). After centrifugation of the reaction, radioactivity in the supernatant is assessed. SULT2A1 activity is expressed as nmoles of sulfate conjugated product formed per hour of incubation. See, Campbell, N. R. C. et al., *Biochem. Pharmacol.*, 36:1435–1446 (1987).

Other biochemical properties of allozymes, such as apparent $K_m$ values, also can be altered relative to the reference SULT2A1 polypeptide. Apparent $K_m$ values can be calculated, for example, by using the method of Wilkinson with a computer program written by Cleland. Wilkinson, *Biochem. J.*, 80:324–332 (1961); and Cleland, *Nature*, 198:463–365 (1963). As described herein, the apparent $K_m$ values for DHEA vary among the allozymes tested.

Polypeptides of the invention can have at least 98% (e.g., 98.5%, 99.0%, 99.5%, or 100%) sequence identity with a region of SEQ ID NO:3 at least 15 amino acids in length (e.g., 20, 30, 40, 50, 60, 70 or more amino acids) and containing one or more variants described herein. For example, a polypeptide can have at least 98% identity with a region of SEQ ID NO:3 containing amino acids 1 to 285, 10 to 100, 20 to 90, 40 to 70, 50 to 70, 110 to 160, 165 to 215, or 220 to 285 of SEQ ID NO:3, wherein the amino acid sequence of SEQ ID NO:3 contains one or more variants described herein. For example, the amino acid sequence of SEQ ID NO3 can include one or more of the following variants: a proline at residue 63, a glutamic acid at residue 227, or a threonine at residue 261.

Percent sequence identity is calculated by determining the number of matched positions in aligned amino acid sequences, dividing the number of matched positions by the total number of aligned amino acids, and multiplying by 100. The percent identity between amino acid sequences therefore is calculated in a manner analogous to the method for calculating the identity between nucleic acid sequences, using the B12seq program from the stand-alone version of BLASTZ containing BLASTN version 2.0.14 and BLASTP version 2.0.14; as indicated above. A matched position refers to a position in which identical residues occur at the same position in aligned amino acid sequences. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. The following command will generate an output file containing a comparison between two amino acid sequences: C:\B12seq -i c:\seq1.txt -j c:\seq2.txt -p blastp -o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive amino acid residues from the target sequence presented in alignment with sequence from the identified sequence starting with any matched position and ending with any other matched position. A matched position is any position where an identical amino acid residue is presented in both the target and identified sequence. Gaps presented in the target sequence are not counted since gaps are not amino acid residues. Likewise, gaps presented in the identified sequence are not counted since target sequence amino acid residues are counted, not amino acid residues from the identified sequence.

The percent identity over a particular length is determined by counting the number of matched positions over that length and dividing that number by the length followed by multiplying the resulting value by 100. For example, if (1) a 100 amino acid target sequence is compared to the sequence set forth in SEQ ID NO:3, (2) the B12seq program presents 20 amino acids from the target sequence aligned with a region of the sequence set forth in SEQ ID NO:3 where the first and last amino acids of that 20 amino acid region are matches, and (3) the number of matches over those 20 aligned amino acids is 18, then the 100 amino acid target sequence contains a length of 20 and a percent identity over that length of 90 (i.e., 18÷20×100=90). As described for aligned nucleic acids, different regions within a single amino acid target sequence that aligns with an identified sequence can each have their own percent identity. It also is noted that the percent identity value is rounded to the nearest tenth, and the length value will always be an integer.

Isolated polypeptides of the invention can be obtained, for example, by extraction from a natural source (e.g., liver tissue), chemical synthesis, or by recombinant production in a host cell. To recombinantly produce SULT2A1 polypeptides, a nucleic acid sequence containing a SULT2A1 nucleotide sequence variant can be ligated into an expression vector and used to transform a bacterial or eukaryotic host cell (e.g., insect, yeast, or mammalian cells). In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems (described above) can be utilized to express SULT2A1 variant polypeptides. A nucleic acid encoding a polypeptide of the invention can be cloned into, for example, a baculoviral vector such as pBlueBac (Invitrogen, San Diego, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides of the invention can be identified by standard methodology.

Mammalian cell lines that stably express SULT2A1 variant polypeptides can be produced by using expression vectors with the appropriate control elements and a selectable marker. For example, the eukaryotic expression vector pCR3.1 (Invitrogen, San Diego, Calif.) and p91023(B) (see Wong et al., *Science* (1985) 228:810–815) are suitable for expression of sulfotransferase variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector as described above, stable cell lines can be selected, e.g., by antibiotic resistance to G418, kanamycin, or hygromycin. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate.

SULT2A1 variant polypeptides can be purified by known chromatographic methods including DEAE ion exchange, gel filtration, and hydroxylapatite chromatography. Van Loon and Weinshilboum, *Drug Metab. Dispos.*, 18:632–638 (1990); Van Loon et al., *Biochem. Pharmacol.*, 44:775–785 (1992). Affinity chromatography is particularly useful for SULT2A1 polypeptides that have been "engineered" to contain an amino acid sequence that allows the polypeptide to be captured onto the affinity matrix. Suitable tags are described above. Immunoaffinity chromatography also can be used to purify SULT2A1 polypeptides.

Non-Human Mammals

The invention features non-human mammals that include SULT2A1 nucleic acids of the invention, as well as progeny and cells of such non-human mammals. Non-human mammals include, for example, rodents such as rats, guinea pigs, and mice, and farm animals such as pigs, sheep, goats, horses and cattle. Non-human mammals of the invention can express a SULT2A1 nucleotide sequence variant in addition to an endogenous SULT2A1 nucleic acid (e.g., a transgenic non-human that includes a SULT2A1 nucleic acid molecule randomly integrated into the genome of the non-human mammal). Alternatively, an endogenous SULT2A1 nucleic acid can be replaced by a SULT2A1 nucleic acid molecule containing a SULT2A1 nucleotide sequence variant through homologous recombination. See, Shastry, B. S., *Mol. Cell Biochem.*, (1998) 181(1–2):163–179, for a review of gene targeting technology.

In one embodiment, non-human mammals are produced that lack an endogenous SULT2A1 nucleic acid (i.e., a knockout), then a SULT2A1 variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous SULT2A1 nucleic acid. That is, cultured ES cells can be transformed with a knockout construct and cells selected in which the SULT2A1 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37–9.52 of Sambrook et al., "Molecular Cloning, A Laboratory Manual," second edition, Cold Spring Harbor Press, Plainview, N.Y., 1989.

To generate a knockout animal, ES cells having at least one inactivated SULT2A1 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated SULT2A1 allele. If the original ES cell was heterozygous for the inactivated SULT2A1 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are "totipotent," i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the SULT2A1 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated endogenous SULT2A1 gene and express a SULT2A1 nucleic acid of the invention, and then fused with enucleated oocytes. After activation of the oocytes, the eggs are cultured to the blastocyst stage, and implanted into a recipient. See, Cibelli, J. B. et al., *Science*, (1998) 280: 1256–1258. Adult somatic cells, including, for example, cumulus cells and mammary cells, can be used to produce animals such as mice and sheep, respectively. See, for example, Wakayama, T. et al., *Nature*, (1998) 394(6691): 369–374; and Wilmut, I. et al., *Nature*, (1997) 385(6619): 810–813. Nuclei can be removed from genetically modified adult somatic cells, and transplanted into enucleated oocytes. After activation, the eggs can be cultured to the 2–8 cell stage, or to the blastocyst stage, and implanted into a suitable recipient. Wakayama, T. et al., 1998, supra.

Non-human mammals of the invention such as mice can be used to screen, for example, toxicity of compounds that are substrates for SULT2A1 polypeptides, drugs that alter SULT2A1 polypeptide activity, or for carcinogenesis. For example, SULT2A1 polypeptide activity or toxicity can be assessed in a first group of such non-human mammals in the presence of a compound, and compared with SULT2A1 polypeptides activity or toxicity in a corresponding control group in the absence of the compound. As used herein, suitable compounds include biological macromolecules such as an oligonucleotide (RNA or DNA) or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally and parenterally. For example, the compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols. Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

Detecting SULT2A1 Sequence Variants

SULT2A1 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., 1995, *Nat. Biotechnol.* 15:33–39), denaturing high performance liquid chromatography (DHPLC, Underhill et al., 1997, *Genome Res.*, 7:996–1005), infared matrix-assisted laser desorption/ionization (IR-MALDI) mass spectrometry (WO 99/57318), and combinations of such methods.

Genomic DNA generally is used in the analysis of SULT2A1 nucleotide sequence variants. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega, Madison, Wis.) and the A.S.A.P.Ⓞ Genomic DNA isolation kit (Boehringer Mannheim, Indianapolis, Ind.).

Typically, an amplification step is performed before proceeding with the detection method. For example, exons or introns of the SULT2A1 gene can be amplified then directly sequenced. Dye primer sequencing can be used to increase the accuracy of detecting heterozygous samples.

Allele specific hybridization also can be used to detect SULT2A1 nucleotide sequence variants, including complete haplotypes of a mammal. See, Stoneking et al., 1991, *Am. J. Hum. Genet.*, 48:370–382; and Prince et al., 2001, *Genome Res.*, 11(1):152–162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the SULT2A1 nucleic acid molecule containing a particular SULT2A1 nucleotide sequence variant. Such hybridizations typically are performed under high stringency as some nucleotide sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For SULT2A1 nucleotide sequence variants that introduce a restriction site, restriction digest with the particular restriction enzyme can differentiate the alleles. For SULT2A1 nucleotide sequence variants that do not alter a common restriction site, mutagenic primers can be designed that introduce a restriction site when the variant allele is present or when the wild type allele is present. A portion of SULT2A1 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of SULT2A1 nucleic acid can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al., 2001, *Genome* 11(1):163–169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, SULT2A1 allozymes can be detected by antibodies that have specific binding affinity for that particular allozyme. SULT2A1 allozymes can be produced in various ways, including recombinantly, as discussed above. Host animals such as rabbits, chickens, mice, guinea pigs and rats can be immunized by injection of a particular SULT2A1 allozyme. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a SULT2A1 allozyme and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy," Alan R. Liss, Inc., pp. 77–96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a SULT2A1 allozyme can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science*, 246: 1275 (1989). Once produced, antibodies or fragments thereof are tested for recognition of SULT2A1 allozymes by standard immunoassay methods including ELISA techniques, radioimmunoassays and Western blotting. See, *Short Protocols in Molecular Biology*, Chapter 11, Green Publishing Associates and John Wiley & Sons, Edited by Ausubel, F. M et al., 1992.

Methods of the Invention

As a result of the present invention, it is now possible to determine sulfonator status of a mammal (e.g., a human subject) as well as to determine if a mammal is predisposed to a disease (e.g., heart condition or cancer) or to predict the course of a disease (e.g., progression of HIV). "Sulfonator status" refers to the ability of a mammal to transfer a sulfate group to a substrate (e.g., DHEA). Levels of DHEA have been implicated in a wide range of conditions, including cardiovascular disease, HIV infection, tumor prevention, and aging. See, for example, Barrett-Connor et al., *New Engl. J. Med.* (1986) 315(24):1519–1524; de la Torre, *Clin. Exp. Rheumatol.* (1997) 15(1):87–90; and Barrou et al., *Presse Med.* (1996) 25(38): 1885–9. Determining sulfonator status allows tailoring of particular treatments (e.g., hormone replacement therapy) to a particular patient. For example, determining sulfonator status of a patient can allow the dosage of a drug to be tailored such that the patient receives an appropriate dose.

Predisposition refers to a relative greater risk for a heart condition such as heart attack or stroke, or a cancer (e.g., testicular cancer or an estrogen-dependent cancer such as breast cancer). SULT2A1 catalyzes sulfate conjugation of estrone and 17β-estradiol, which prevents formation of catecholestrogens such as 2-hydroxyestrone, 2-hydroxyestradiol, 4-hydroxyestrone, and 4-hydroxyestradiol. SULT2A1 also can catalyze sulfate conjugation of catecholestrogens, which inactivates the catecholestrogens and diverts the compounds from receptor-mediated and genotoxic pathways of carcinogenesis. Adjei and Weinshilboum, *Biochem. Biophys. Res. Commun.* 292:402–408 (2002). Additional risk factors for heart conditions and cancer, including, for example, family history of heart disease or cancer and other genetic factors, can be considered when determining risk.

Sulfonator status and predisposition to a heart condition or cancer can be determined based on the presence or absence of a single sulfotransferase sequence variant or based on a variant profile. "Variant profile" refers to the presence or absence of a plurality (i.e., two or more sequence variants) of SULT2A1 nucleotide sequence variants or SULT2A1 amino acid sequence variants. For example, a variant profile can include the complete SULT2A1 haplotype of the mammal or can include the presence or absence of a set of common SNPs (e.g., one or more common non-synonymous SNPs that alter the amino acid sequence of a SULT2A1 polypeptide). In one embodiment, the variant profile includes detecting the presence or absence of two or more non-synonymous SNPs (e.g., 2 or 3 non-synonymous SNPs) described above. There may be ethnic-specific pharmacogenetic variation, as certain of the nucleotide and amino acid sequence variants described herein were detected solely in African-American subjects. For example, a common haplotype in samples from African-American subjects includes the three SNPs at −122, 187, and 781 relative to the adenine of the SULT2A1 translation initiation codon. In addition, the variant profile can include detecting the presence or absence of any type of SULT2A1 SNP together with any other SULT2A1 SNP (i.e., a polymorphism pair or groups of polymorphism pairs). Such polymorphism pairs include, without limitation, those pairs described in Table 4.

Articles of Manufacture

Articles of manufacture of the invention include populations of isolated SULT2A1 nucleic acid molecules or SULT2A1 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different SULT2A1 nucleotide or SULT2A1 amino acid sequence variant. Such articles of manufacture can include two or more nucleotide or amino acid sequence variants, or can include all of the sequence variants known for SULT2A1. Furthermore, nucleic acid molecules containing sequence variants for other sulfotransferases, such as SULT1A1, SULT1A2, SULT1A3, and SULT1A2, can be included on the substrate. See, WO 99/64630 and WO 00/20605 for a description of other SULT1A1, SULT1A2, SULT1A3, and SULT1A2 sequence variants.

Suitable substrates can be of any shape or form and can be constructed from, for example, glass, silicon, metal, plastic, cellulose or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., *Nature Genet.*, 14:441–447 (1996); and U.S. Pat. Nos. 5,770,722 and 5,733,729.

The invention will be further described in the following examples, which do not limit the scope of the invention described in the claims.

EXAMPLES

Example 1

Methods and Materials: PCR Amplification and DNA Sequencing

Blood samples were obtained from 60 randomly selected African American blood donors and 60 randomly selected Caucasian blood donors at the Mayo Clinic Blood Bank in Rochester, Minn. Genomic DNA was extracted from each blood sample using QIAamp Blood Kits (Qiagen, Valencia, Calif.). Once extracted, the genomic DNA was used as template in a PCR with SULT2A1-specific primers. The 6 exons in the SULT2A1 gene were amplified from each of the 120 DNA samples using primers that flanked the exons and that would produce amplification products 400–500 bp in length. Amplification of the entire gene required seven separate reactions for each DNA sample. The hybridization location of each primer was chosen to avoid repetitive sequence and to ensure amplification specificity. All forward primers contained the M13 forward sequence, and all reverse primers contained the M13 reverse sequence for use in dye primer DNA sequencing. The sequences and locations of each primer within the gene are listed in Table 1 ("F" represents forward; "R", reverse; "U", upstream; "D", downstream; "I", intron; "FR", flanking region; and "UTR", untranslated region).

Following amplification, the products from each reaction were sequenced using dye primer DNA sequencing chemistry to identify heterozygous bases. DNA sequencing was performed in the Mayo Clinic Molecular Biology Core Facility with an Applied Biosystems Model 377 DNA sequencers and BigDye™ (Perkin Elmer, Foster City, Calif.) dye primer sequencing chemistry. In all cases, both DNA strands were sequenced.

DNA sequence analysis: The seven separate SULT2A1 PCR amplifications performed for each of the 120 individual human genomic DNA samples described above generated a total of approximately 600,000 bp of sequence. The DNA chromatograms for this sequence were analyzed both visually and using PolyPhred 3.0, Consed 8.0, and GCG 10.0 software. All sequences were compared to the SULT2A1 gene sequences of GenBank accession numbers U13056, U13057, U13058, U13059, U13060, and U13061.

COS-1 cell expression: Five different SULT2A1 expression constructs were made using the pCR3.1 expression vector. Four of the constructs were designed to express SULT2A1 allozymes, while the remaining construct was designed to express a wild type SULT2A1 polypeptide. All SULT2A1 cDNA sequences containing SULT2A1 nucleotide sequence variants used to create the expression constructs were created by site directed mutagenesis using the method described by Ho et al., *Gene* 77(1):51–9 (1989). Each SULT2A1 cDNA was amplified by PCR and subcloned into the eukaryotic expression vector pCR3.1 (Promega, Madison, Wis.). After subcloning, all inserts were sequenced to assure that no spurious nucleotide point mutations had been introduced during the PCR amplifications. COS-1 cells were transfected with these expression constructs by the TransFast○ reagent (Promega, Madison, Wis.) as suggested by the manufacturer (i.e., using a 1:1 charge ratio). As a control, a transfection was also performed with "empty" pCR3.1, i.e., vector lacking an insert, to make it possible to correct for endogenous COS-1 cell SULT activity. The control plasmid pSV-β-galactosidase (Promega) was cotransfected with each SULT2A1 construct to make it possible to correct for transfection efficiency. Two independent transfections, each consisting of three separate plates, were performed with each of the expression constructs. After 48 hours in culture, the transfected cells were harvested and high speed supernatant (HSS) cytosol preparations were prepared as described by Wood, T. C. et al., *Biochem. Biophys. Res. Commun.*, 198:1119–1127 (1994). Aliquots of these cytosol preparations were stored at −80° C. prior to assay.

Enzyme Assays: β-galactosidase activity in each of the COS-1 HSS preparations was measured with the β-galactosidase Enzyme Assay System (Promega, Madison, Wis.). These HSS preparations of recombinant SULT2A1 allozymes were used for the activity studies without any further purification. The protein concentration of each recombinant protein preparation was determined by the dye-binding method of Bradford with bovine serum albumin (BSA) as a standard.

SULT2A1 enzyme activity was measured with an assay that involves sulfate conjugation of a sulfate acceptor substrate, DHEA, in the presence of the sulfate donor 3'-phosphoadenosine-5'-phosphosulfate (PAPS). See, Campbell, N. R. C. et al., *Biochem. Pharmacol.*, 36:1435–1446 (1987). Briefly, 0.4 μM $^{35}$S-PAPS and a HSS preparation were reacted with 5 μM DHEA in 5 mM potassium phosphate buffer at pH 6.5. Blanks were samples that did not contain DHEA. Cytosol from COS-1 cells that had been transfected with empty pCR3.1 was used to correct for endogenous SULT activity. Because SULTs display profound substrate inhibition, DHEA concentrations that ranged from 100 pM to 1 mM were tested with each recombinant allozyme to ensure that the assays were performed at DHEA concentrations that yielded maximal activity for that allozyme. Enzyme activity was expressed as nanomoles (nmoles) of sulfate conjugated product formed per hour of incubation. Apparent $K_m$ values for PAPS were determined in the presence of 5 μM DHEA with six PAPS concentrations that varied from 0.0625 μM to 2 μM.

Western blot analysis: Levels of immunoreactive SULT2A1 were determined for each recombinant allozyme by performing quantitative Western blot analysis. Rabbit polyclonal antibody directed against SULT2A1 amino acids 268–285, with an additional amino terminus cysteine (described in Wood et al., *J. Steroid Biochem. Mol. Biol.* 59:467–478 (1996)) at a dilution of 1:2000 was used in these studies. Specifically, recombinant protein was loaded on a 12% SDS mini-gel (BioRad, Hercules, Calif.) in quantities that resulted in equal β-galactosidase activity, i.e., gel loading was corrected for variation in transfection efficiency. Electrophoresis was performed for 1 h at 150 volts, and proteins were transferred to nitrocellulose membranes. The membranes were blocked overnight at 4° C. with 5% dried milk in Tris buffered saline with Tween-20 (TBST). Subsequently, the membranes were incubated with primary antibody for 1 h, followed by three TBST washes. The secondary antibody, a 1:10,000 dilution of goat anti-rabbit horseradish peroxidase (BioRad), was applied for 1 h in 5% milk in TBST, followed by multiple washes. Bound antibody was detected with the ECL Western Blotting System (Amersham Pharmacia, Piscataway, N.J.). Multiple blots were assayed for each allozyme, and immunoreactive protein levels were expressed as a percentage of the intensity of the control wild type SULT2A1 protein band on the same gel. The AMBIS Radioanalytical Imaging System, Quant Probe v. 4.31 (AMBIS, San Diego, Calif.) was used to analyze each blot.

Gel Filtration Chromatography: Gel filtration chromatography of recombinant human SULT2A1 was performed at 4° C. with a 2×25 cm column of Sephadex G-100 superfine. The mobile phase was 5 mM K phosphate buffer, pH 7.5, and 3 ml fractions were collected at a flow rate of approximately 1.8 mL per h. The fractions were assayed for SULT2A1 activity. Standards for column calibration were eluted separately and included Dextran Blue 2000, bovine serum albumin (67 kDa), ovalbumin (45 kDa), chymotrypsinogen A (20 kDa) and ribonuclease A (13.7 kDa).

Data Analysis: Average levels of enzyme activity were compared by ANOVA, using the StatView program, version 4.5 (Abacus Concepts, Inc., Berkeley, Calif.). Apparent $K_m$ values were calculated by using the method of Wilkinson with a computer program written by Cleland. Wilkinson, G. N., *Biochem. J.*, 80:324–332 (1961); and Cleland, W. W., *Nature*, 198:463–365 (1963). Apparent Km values were compared by the use of unpaired Student's t-test. Linkage analysis involved testing all possible pairwise combinations of SNPs by calculating D' values using the methods of Hartl and Clark, *Principles of Population Genetics* 3$^{rd}$ edn. Sinauer Associates: Sunderland, Mass., 1997, pp. 95–107; and Hedrick, *Genetics of Populations* 3$^{rd}$ edn. Jones and Bartlett Publ: Sudbury, Mass., 2000, pp. 396–405.

TABLE 1

PCR primers used for resequencing SULT2A1

| Primer Name | Primer Location | Primer Sequence Gene Specific Primer-3' | SEQ ID NO: |
|---|---|---|---|
| F(−370)M13 | 5'-FR | TGTAAAACGACGGCCAGTGCTTTGTTCTTGTTTTTAAGTTTGCAC | 4 |
| R(−44)M13 | | CAGGAAACAGCTATGACCCACCGCTGGAGGCTGTGGCAGCTACAG | 5 |
| F(−118)M13 | Exon 1 | TGTAAAACGACGGCCAGTGGGACAAGGTTAAAGATCGTTTTATC | 6 |
| I1R103M13 | | CAGGAAACAGCTATGACCAAGCATTGTACACTGTCTGAC | 7 |
| I1F(−50)M13 | Exon 2 | TGTAAAACGACGGCCAGTATGTCCGGCTGAGATGGTACA | 8 |
| I2R112M13 | | CAGGAAACAGCTATGACCAACACAGACCTGTTGAAGGAG | 9 |
| I2F(−112)M13 | Exon 3 | TGTAAAACGACGGCCAGTATTGATATTATTAGGCATTATCCA | 10 |
| I3R129M13 | | CAGGAAACAGCTATGACCAGGTTTGGCCTCCAGGGGTGG | 11 |
| I3F(−176)M13 | Exon 4 | TGTAAAACGACGGCCAGTACATCTGTTATATACTGTAAA | 12 |
| I4R94M13 | | CAGGAAACAGCTATGACCGGTGGAATGAAGACACAG | 13 |
| I4F(−76)M13 | Exon 5 | TGTAAAACGACGGCCAGTGGGATTACACGGTGAACCACC | 14 |
| I5R98M13 | | CAGGAAACAGCTATGACCAAGCTCTCTTTCATCTCAACT | 15 |
| I5F(−95)M13 | Exon 6 | TGTAAAACGACGGCCAGTCTGCTATGTTAGCTACAATGTCCA | 16 |
| R361M13 | | CAGGAAACAGCTATGACCTTTTAACAAGGAAGGGATCAG | 17 |

Underlined nucleotides indicate M13 tag

Example 2

SULT2A1 Polymorphisms: Sequencing of the 5' and 3' untranslated sequences, exons, and introns of the SULT2A1 nucleic acid revealed 15 SNPs (Table 2). Polymorphisms in exons, untranslated regions (UTR), and flanking regions (FR) are numbered relative to the adenine in the SULT2A1 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1). Three of the 15 SNPs altered the encoded amino acid (i.e., a non-synonymous SNP), resulting in three different SULT2A1 allozymes. Two of the three variants appeared to be "common" (frequency≧1%, Table 2) among the 60 African American samples. The same three variants were not detected among the 60 Caucasian samples.

The average number of polymorphisms present in the gene overall, within the ORF, and outside the ORF was 5.6, 8.7, and 5.0 per kb sequenced, respectively, in the African American samples (Table 3). The average number of polymorphisms present in the gene overall and within the ORF was 2.4, 0, and 3.8 per kb sequenced, respectively, in the Caucasian samples (Table 3). For purposes of comparison, Table 3 also includes data from a large study of polymorphism frequencies in 74 human genes (Halushka et al., *Nat. Genet.* (1999) 22(3):239–247). Because Halushka et al. studied a slightly smaller number of samples (74 versus the 120 described), low frequency polymorphisms that would not have been detected by Halushka et al. have been eliminated because of their lower sample number. The genetic variation present within the SULT2A1 sequence was very similar to average values observed in the 74 genes sequenced by Halushka et al. The data in Table 3 are also presented by gene region, with "UTR" representing both exons encoding cDNA untranslated regions and 5'- and 3'-flanking regions.

TABLE 3

SULT2A1 polymorphism frequencies

Polymorphisms per kb

SULTA1

| | African American | Caucasian | 74 Human Genes |
|---|---|---|---|
| Gene(s) | 1 | 1 | 74 |
| Samples | 60 | 60 | 75 |
| Min. Allele Freq. | 0.80% | 0.80% | 0.68% |
| Overall | 5.6 | 2.4 | 4.6 |
| Coding | 8.7 | 0.0 | 4.4 |
| Noncoding | 5.0 | 3.8 | 5.9 |
| UTRs | 7.4 | 3.7 | 4.4 |
| Introns | 6.0 | 5.0 | 6.0 |

Example 3

Linkage disequilibrium analysis: Linkage disequilibrium analysis was performed after all of the DNA samples had been genotyped at each of the 15 polymorphic sites. Pairwise combinations of these polymorphisms were tested for linkage disequilibrium using the EH program developed by Terwilliger and Ott, *Handbook of Human Genetic Linkage*, The Johns Hopkins University Press, Baltimore, pp. 188–193 (1994). The output of this program was used to calculate d' values, a method for reporting linkage data that is independent of sample size. D' values can range from +1.0 when two polymorphisms are maximally positively associated, to −1.0 when two polymorphisms never occur together. All pairwise combinations with a linkage disequilibrium greater than or equal to 1% are shown in Table 4. Seven pairs of SNPs had statistically significant Chi-square values (>3.84) for D', and the three polymorphisms at nucleotides −122, 187, and 781 had absolute D' values which were greater than 0.3. In all three of those cases, D' was 1.0—i.e.,

TABLE 2

Human SULT2A1 sequence variants

| Position | Location | Nucleotide Wild Type Allele | Nucleotide Variant Allele | Altered Amino Acid | Frequency of Variant African-American | Frequency of Variant Caucasian |
|---|---|---|---|---|---|---|
| −122 | 5'-FR | G | A | | 0.042 | 0.000 |
| 6 | Exon 1 | G | A | | 0.017 | 0.000 |
| 90 | Exon 1 | C | T | | 0.067 | 0.000 |
| 11(16) | Intron 1 | C | T | | 0.033 | 0.167 |
| 187 | Exon 2 | G | C | Ala63Pro | 0.050 | 0.000 |
| 258 | Exon 2 | A | C | | 0.008 | 0.000 |
| 12(34) | Intron 2 | G | A | | 0.100 | 0.017 |
| 13(57) | Intron 3 | C | T | | 0.008 | 0.000 |
| 13(−129) | Intron 3 | G | A | | 0.050 | 0.083 |
| 13(−94) | Intron 3 | C | G | | 0.092 | 0.283 |
| 14(67) | Intron 4 | C | T | | 0.008 | 0.033 |
| 679 | Exon 5 | A | G | Lys227Glu | 0.008 | 0.000 |
| 781 | Exon 6 | G | A | Ala261Thr | 0.133 | 0.000 |
| 924 | Exon 6 | T | C | | 0.000 | 0.017 |
| 935 | Exon 6 | A | T | | 0.058 | 0.000 | all three of these SNPs were highly linked, even though one was located in the 5' flanking region, one was in exon 2, and the final SNP was in exon 6. That is, the polymorphisms were spread over a total length of approximately 14.7 kB. It should be noted that the SNPs at nucleotides 187 and 781 were non-synonymous, with frequencies in DNA samples from African American subjects of 0.05 and 0.137, respectively. Thus, a common haplotype in samples from African American DNA subjects includes all three of these SNPs.

TABLE 4

SULT2A1 linkage disequilibrium analysis

| Polymorphism Pair | | d' Value | $\chi^2$ Value |
|---|---|---|---|
| 781 | 935 | +1.000 | 31.65 |
| 187 | 781 | +1.000 | 26.63 |
| −122 | 187 | +1.000 | 36.27 |
| −122 | 781 | +1.000 | 21.80 |
| 90 | I2(34) | +0.300 | 3.96 |
| 90 | I3(−94) | −0.225 | 3.39 |
| I2(34) | I3(−94) | −0.231 | 6.01 |
| I3(−94) | 781 | −0.230 | 4.13 |
| −122 | 90 | −0.034 | 0.34 |
| −122 | I1(16) | −0.111 | 1.07 |
| −122 | I2(34) | −0.062 | 0.61 |
| −122 | I3(−129) | −0.071 | 0.70 |
| −122 | I3(−94) | −0.225 | 0.71 |
| −122 | I4(67) | −0.021 | 0.21 |
| −122 | 935 | −0.030 | 0.30 |
| 90 | I1(16) | −0.093 | 0.34 |
| 90 | 187 | −0.034 | 0.41 |
| 90 | I3(−129) | −0.009 | 0.01 |
| 90 | I4(67) | −0.034 | 0.34 |
| 90 | 781 | −0.071 | 1.12 |
| 90 | 935 | −0.034 | 0.48 |
| I1(16) | 187 | −0.111 | 1.28 |
| I1(16) | I2(34) | −0.111 | 1.65 |
| I1(16) | I3(−129) | −0.111 | 3.50 |
| I1(16) | I3(−94) | −0.167 | 0.99 |
| I1(16) | I4(67) | −0.111 | 1.07 |
| I1(16) | 781 | −0.111 | 3.50 |
| I1(16) | 935 | −0.111 | 1.50 |
| 187 | I2(34) | −0.062 | 0.73 |
| 187 | I3(−129) | −0.071 | 0.84 |
| 187 | I3(−94) | −0.229 | 1.13 |
| 187 | I4(67) | −0.026 | 0.26 |
| 187 | 935 | −0.030 | 0.36 |
| I2(34) | I3(−129) | −0.071 | 1.99 |
| I2(34) | I4(67) | +0.096 | 0.30 |
| I2(34) | 781 | −0.071 | 1.99 |
| I2(34) | 935 | −0.062 | 0.085 |
| I3(−129) | I3(−94) | −0.218 | 1.35 |
| I3(−129) | I4(67) | −0.071 | 0.70 |
| I3(−129) | 781 | −0.070 | 0.89 |
| I3(−129) | 935 | −0.071 | 0.98 |
| I3(−94) | I4(67) | −0.231 | 2.10 |
| I3(−94) | 935 | −0.229 | 1.56 |
| I4(67) | 781 | −0.071 | 0.70 |
| I4(67) | 935 | −0.030 | 0.30 |

Example 4

Activity of SULT2A1 Allozymes: Catalytic activity of cytosol preparations of recombinant SULT2A1 allozymes, prepared as described in Example 1, were used to assess catalytic activity in the presence of 5 μM DHEA. The resulting activities were adjusted to a percentage of the WT SULT2A1 enzyme activity.

In addition, the apparent $K_m$ values for each enzyme were determined using PAPS. Because SULTs, including SULT2A1, can show profound substrate inhibition, experiments involving the sulfate acceptor cosubstrate were conducted in two stages. Initially, a wide range of concentrations was tested followed by a determination of $K_m$ values within a narrower range of concentrations. Although there were statistically significant variations among the allozymes in apparent $K_m$ values for both DHEA and PAPS, those variations were not large quantitatively, and in the case of PAPS the apparent $K_m$ values for three of the variant allozymes were significantly lower than that of the WT enzyme (Table 5). As a result, decreases in the level of enzyme activity observed for three of the four variant allozymes could not be attributed entirely to alterations in substrate affinity.

Quantitative Western blot analysis showed that levels of immunoreactive SULT2A1, corrected for transfection efficiency, paralleled relative levels of enzyme activity among the variant allozymes (Table 5). Western blot analysis data were obtained by assaying cytosol for each allozyme from three independent transfections performed on different days to ensure that results were reproducible. The data listed in Table 5 are averages of those three transfections. Table 5 also lists the ratio of enzymatic activity to immunoreactive protein for each allozyme. It should be noted that none of the alterations in encoded amino acid for the variant allozymes studied were located within the sequence of the peptide used to generate the rabbit polyclonal antibody utilized to perform the Western blots. These studies showed that alterations in the amino acid sequence of SULT2A1 as a result of genetic polymorphisms significantly altered levels of enzyme protein.

TABLE 5

Human SULT2A1 functional genomic studies

| Construct | Enzyme Activity (%) | Immunoreactive protein (%) | Enzyme activity: immunoreactive protein | DHEA $K_m$ (μM) | PAPS $K_m$ (nM) |
|---|---|---|---|---|---|
| WT | 100 | 100 | 1.0 | 0.247 ± 0.071 | 21.8 ± 0.86 |
| Ala63Pro | 57 ± 7* | 27 ± 9* | 2.1 | 0.210 ± 0.010 | 8.2 ± 1.32* |
| Lys227Glu | 15 ± 3* | 2 ± 1* | 7.5 | 0.905 ± 0.053* | 10.2 ± 0.96* |
| Ala261Thr | 93 ± 6 | 79 ± 7 | 1.2 | 0.245 ± 0.012 | 22.7 ± 0.62 |
| 63Pro/261Thr | 42 ± 2* | 26 ± 14* | 1.6 | 0.290 ± 0.012 | 11.4 ± 0.30* |

*Values differ significantly from WT enzyme (P < 0.05)

Three of the four recombinant SULT2A1 allozymes had significantly decreased enzyme activity, after correction for transfection efficiency, as compared to that of the WT sequence Table 5). Recombinant enzyme containing the Ala63Pro change, a polymorphism with a frequency of 0.05 in African-American subjects, resulted in only 57% of the average activity present compared to wild-type enzyme. When the Ala63Pro polymorphism was combined with Ala261Thr, thus creating the double variant that occurred commonly in the African-American subjects studied, enzyme activity was decreased to 42% of the wild-type level (Table 5). However, activity of the Ala261Thr variant alone, an allozyme encoded by approximately 8% of all alleles in African-American subjects, (85% reduction, or 15% of WT activity; Table 5), resulted in the largest decrease in activity.

Example 5

SULT2A1 Crystal Structure and Dimerization: The x-ray crystal structure of SULT2A1 has been solved at a resolution of 2.3 Å, enabling the locations of polymorphic SULT2A1 amino acids within that structure to be determined. The polymorphism that resulted in the Ala63Pro change in amino acid was located 14 residues downstream from the conserved 'Region I' sequence motif that is present in all known human SULTs and which is thought to be involved in PAPS binding. That change in amino acid resulted in a 43% decrease in enzyme activity as well as a decrease in immunoreactive protein (Table 5). This amino acid was located on the 'surface' of the protein. Lys227Glu was located four amino acids upstream of the putative SULT2A1 substrate-binding site. Like Ala63Pro, this residue was also on the surface of the protein. This latter alteration in sequence resulted in a striking decrease in enzyme activity (to 15% of the activity of the wild-type sequence) as well as a very low level of immunoreactive protein (Table 5).

The Ala261 Thr polymorphism is located within the dimerization motif at the C-terminus of the conserved 'Region IV' SULT signature sequence, and may alter the formation of the SULT2A1 homodimer. To test that hypothesis, recombinant WT and codon Thr261 variant allozyme preparations were subjected to gel filtration chromatography through Sephadex G-100. Those experiments showed that the major peak for WT enzyme was compatible with the presence of SULT2A1 dimer, while that for the variant allozyme was compatible with monomer. As a result, this appears to be the first demonstration of a common SULT genetic polymorphism that disrupts dimerization.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting essentially of a variant SULT2A1 nucleic acid sequence, wherein said variant SULT2A1 nucleic acid sequence is selected from the group consisting of:
   a) at least 10 contiguous nucleotides of SEQ ID NO:18, wherein said sequence includes nucleotide 1718 of SEQ ID NO:18, with the proviso that the nucleotide at position 1718 is adenine;
   b) at least 10 contiguous nucleotides of SEQ ID NO:2, wherein said sequence includes nucleotide 207 of SEQ ID NO:2, with the proviso that the nucleotide at position 207 is cytosine;
   c) at least 10 contiguous nucleotides of SEQ ID NO:2, wherein said sequence includes nucleotide 699 of SEQ ID NO:2, with the proviso that the nucleotide at position 699 is guanine;
   d) at least 10 contiguous nucleotides of SEQ ID NO:2, wherein said sequence includes nucleotide 801 of SEQ ID NO:2, with the proviso that the nucleotide at position 801 is adenine; and
   e) the complement of (a), (b), (c), or (d).

2. The isolated nucleic acid of molecule of claim 1, wherein said isolated nucleic acid molecule is from 10 to 100 nucleotides in length.

3. The isolated nucleic acid of molecule of claim 1, wherein said isolated nucleic acid molecule is from 20 to 50 nucleotides in length.

4. A vector comprising the nucleic acid molecule of claim 1.

5. The vector of claim 4, wherein said nucleic acid molecule is from 20 to 50 nucleotides in length.

* * * * *